US008632777B2

(12) United States Patent
Elsässer-Beile et al.

(10) Patent No.: US 8,632,777 B2
(45) Date of Patent: *Jan. 21, 2014

(54) MONOCLONAL ANTIBODIES AND SINGLE CHAIN ANTIBODY FRAGMENTS AGAINST CELL-SURFACE PROSTATE SPECIFIC MEMBRANE ANTIGEN AS DIAGNOSTIC AND THERAPEUTIC TOOLS FOR PROSTATE CANCER

(75) Inventors: Ursula Elsässer-Beile, Denzlingen (DE); Philipp Wolf, Gundelfingen (DE); Dorothee Gierschner, Teningen (DE); Patrick Bühler, Freiburg (DE); Ulrich Wetterauer, Freiburg (DE)

(73) Assignee: Universitätsklinikum Freiburg, Freiburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/466,286

(22) Filed: May 8, 2012

(65) Prior Publication Data

US 2012/0231024 A1  Sep. 13, 2012

Related U.S. Application Data

(62) Division of application No. 11/915,454, filed as application No. PCT/EP2006/001917 on Mar. 2, 2006, now Pat. No. 8,198,416.

(30) Foreign Application Priority Data

May 27, 2005  (EP) .................................... 05011536

(51) Int. Cl.
*A61K 38/00* (2006.01)
(52) U.S. Cl.
USPC .................. 424/141.1; 424/135.1; 424/136.1; 424/184.1; 530/387.1; 530/388.2
(58) Field of Classification Search
None
See application file for complete search history.

(56) References Cited

U.S. PATENT DOCUMENTS

| 6,255,458 | B1 | 7/2001 | Lonberg et al. |
| 6,258,939 | B1 | 7/2001 | Reiter et al. |
| 8,198,416 | B2 * | 6/2012 | Elsasser-Beile et al. .. 530/391.7 |
| 2003/0161832 | A1 * | 8/2003 | Bander ...................... 424/155.1 |
| 2004/0213791 | A1 | 10/2004 | Bander et al. |
| 2004/0242851 | A1 * | 12/2004 | Zhu .......................... 530/388.22 |
| 2007/0036719 | A1 | 2/2007 | Cuello et al. |
| 2009/0041789 | A1 | 2/2009 | Elsaesser-Beile et al. |

FOREIGN PATENT DOCUMENTS

| WO | WO 97/35616 | 10/1997 |
| WO | WO 98/03873 | 1/1998 |
| WO | WO 01/09192 | 2/2001 |
| WO | WO 03/002144 | 1/2003 |

OTHER PUBLICATIONS

Lazar et al (Mol Cell Biol, 1998, 8:1247-1252).*
Burgess et al (J Cell Biol, 1990, 111:2129-2138).*
Padlan et al (FASEB J, 1995, 9:133-139).*
Lum et al (Anticancer Research, 2005, 25:43-52).*
Abraham, R., et al., "Determination of Binding Constants of Diabodies Directed against Prostate-specific Antigen using Electrochemiluminescence-based Immunoassays," J. Mol. Recog. 1996;9:456-461.
Bander, N. H., et al., "Targeted Systemic Therapy of Prostate Cancer With a Monoclonal Antibody to Prostate-Specific Membrane Antigen," Sem. Oncol. 2003;30(5):667-677.
Davies, J., et al., "Affinity improvement of single antibody VH domains: residues in all three hypervariable regions affect antigen binding," Immunotechnol. 1996;2:169-179.
Fracasso, G., et al., "Anti-tumor Effects of Toxins Targeted to the Prostate Specific Membrane Antigen," The Prostate 2002;53:9-23.
Holt, L. J., et al., "Domain antibodies: proteins for therapy," Trends in Biotechnol. 2003;21(11):484-490.
Katzenwadel, A., et al., "Construction and in Vivo Evaluation of an Anti-PSA x Anti-CD3 Bispecific Antibody for the Immunotherapy of Prostate Cancer," Anticancer Res. 2000;20:1551-1556.
International Search Report and Written Opinion of the International Searching Authority for PCT Patent App. No. PCT/EP2006/001917 (Jun. 1, 2006).
Burgess, Shaheen, Raver, Jaye, Donohue, and Winkles. Possible dissociation of the heparin-binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.
Rudikoff, Giusti, Cook, and Scharff. Single amino acid substitution altering antigen-binding specificity. Proceedings of the National Academy of Sciences, 1982. vol. 79, pp. 1979-1983.
Mac Callum, Martin, and Thornton. Antibody-antigen interactions: contact analysis and binding site topography. Journal of Molecular Biology, 1996. vol. 262, pp. 732-745.
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.

(Continued)

*Primary Examiner* — Sean Aeder
*Assistant Examiner* — Julie Wu
(74) *Attorney, Agent, or Firm* — Shelly Guest Cermak; Cermak Nakajima LLP

(57) ABSTRACT

Isolated monoclonal antibodies or an antigen binding portion thereof which bind to prostate specific membrane antigen in its native form occurring on the surface of tumor cells characterized in that it is linked to a label or a cytotoxic agent or constructed as a part of a bispecific antibody or a recombinant diabody.

6 Claims, 25 Drawing Sheets

(56) References Cited

OTHER PUBLICATIONS

Holm, Jafari, and Sundstrom. Functional mapping and single chain construction of the anti-cytokeratin 8 monoclonal antibody TS1. Molecular Immunology, 2007. vol. 44, pp. 1075-1084.

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.

Wu, Nie, Huse, and Watkins. Humanization of a murine monoclonal antibody by simultaneous optimization of framework and CDR residues. Journal of Molecular Biology, 1999. vol. 294, pp. 151-162.

Elsasser-Belle, Wolf, Gierschner, Buhler, Schultze-Seemann, and Wetterauer. A new generation of W monoclonal and recombinant antibodies against cell-adherent prostate specific membrane antigen for diagnostic and therapeutic targeting of prostate cancer. The Prostate, 2006. vol. 66, pp. 1359-1370.

Smith-Jones, Vallabhajosula, Navarro, Bastidas, Goldsmith, and Bander. Radiolabeled monoclonal antibodies specific to the extracellular domain of prostate-specific membrane antigen: preclinical studies in nude mice bearing LNCaP human prostate tumor. Journal of Nuclear Medicine, 2003. vol. 44, pp. 610-617.

Bühler, P., et al., "Influence of Structural Variations on Biological Activity of Anti-PSMA scFv and Immunotoxins Targeting Prostate Cancer," Anticancer Res. 2010;30:3373-3380.

Chang, S. S., et al., "Five Different Anti-Prostate-specific Membrane Antigen (PSMA) Antibodies Confirm PSMA Expression in Tumor-associated Neovasculature," Cancer Res. 1999;59:3192-3198.

Holland, J. P., et al., "$^{89}$Zr-DRO-J591 for ImmunoPET of Prostate-Specific Membrane Antigen Expression in Vivo," J. Nucl. Med. 2010;51:1293-1300.

Israeli, R. S., et al., "Expression of the Prostate-specific Membrane Antigen," Cancer Res. 1994;54:1807-1811.

Liu, H., et al., "Monoclonal Antibodies to the Extracellular Domain of Prostate-specific Membrane Antigen Also React with Tumor Vascular Endothelium," Cancer Res. 1997;57:3629-3634.

Santana, S. M., et al., "Immunocapture of prostate cancer cells by use of anti-PSMA antibodies in microdevices," Biomed Microdevices 2012;14:401-407.

Schülke, N., et "The homodimer of prostate-specific membrane antigen is a functional target for cancer therapy," PNAS 2003;100(22):12590-12595.

Silver, D. A., et al., "Prostate-specific Membrane Antigen Expression in Normal and Malignant Human Tissues," Clin. Cancer Res. 1997;3:81-85.

Troyer, J. K., et al., "Detection and Characterization of the Prostate-Specific Membrane Antigen (PSMA) in Tissue Extracts and Body Fluids," Int. J. Cancer 1995;62:552-558.

Wolf, P., et al., "Three Conformational Antibodies Specific for Different PSMA Epitopes Are Promising Diagnostic and Therapeutic Tools for Prostate Cancer," the Prostate 2010;70:562-569.

\* cited by examiner

Fig 1a-c

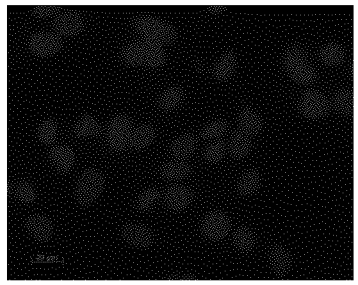
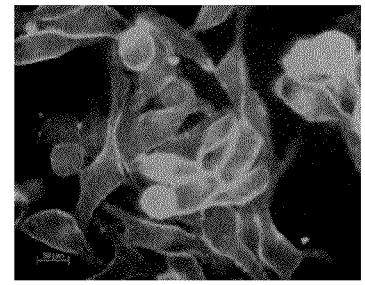
3/F11
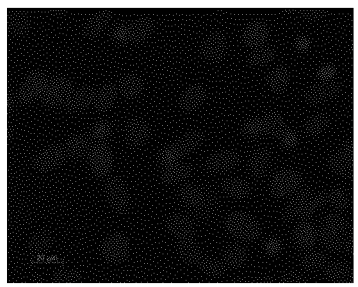
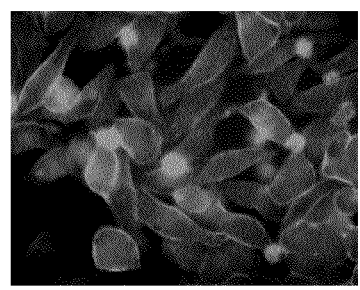
3/A12
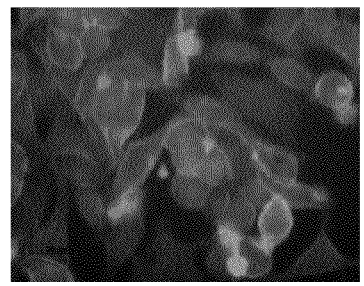
3/E7
Fig 2

3/F11
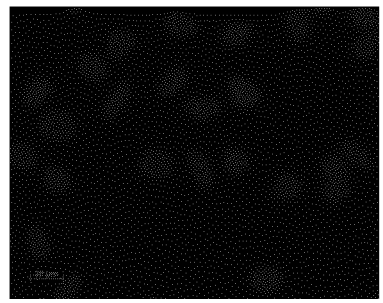 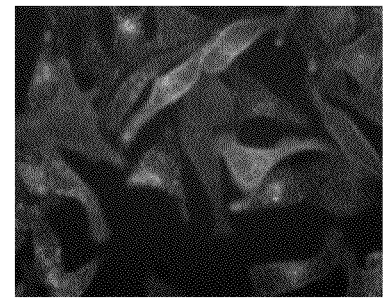
3/A12
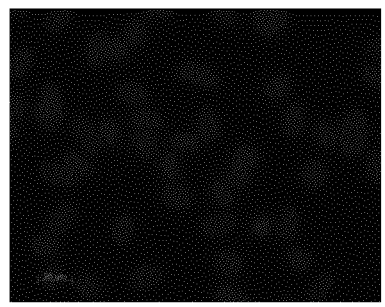 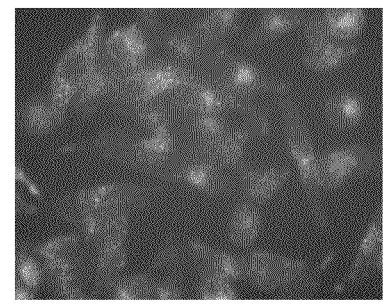
3/E7
Fig 3

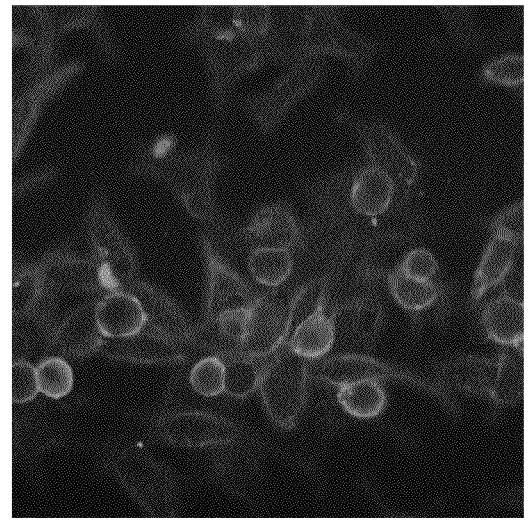
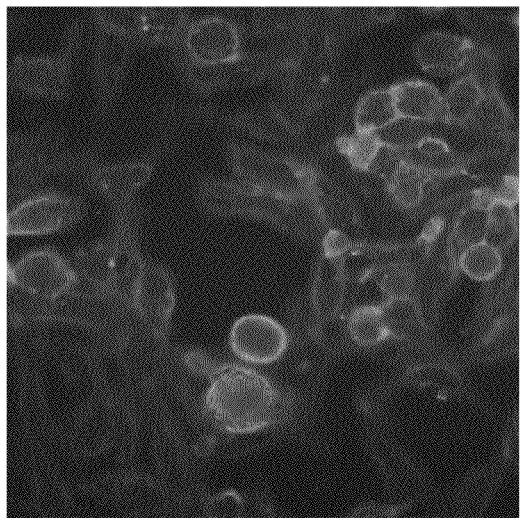
Fig 9

```
      M   A   E   V   Q   L   Q   Q   S   G   P   D   L   V   K   P   G   A
  1   ATG GCC GAG GTG CAG CTG CAG CAG TCA GGA CCC GAC CTG GTG AAG CCT GGG GCC
      TAC CGG CTC CAC GTC GAC GTC GTC AGT CCT GGG CTG GAC CAC TTC GGA CCC CGG
      S   M   K   I   S   C   K   A   S   G   Y   T   F   T   D   Y   N   M
 55   TCA ATG AAG ATT TCC TGC AAG GCT TCT GGA TAC ACA TTC ACT GAC TAC AAC ATG
      AGT TAC TTC TAA AGG ACG TTC CGA AGA CCT ATG TGT AAG TGA CTG ATG TTG TAC
      D   W   V   K   E   R   H   G   K   S   L   E   W   I   G   D   I   N
109   GAC TGG GTG AAG GAG AGA CAT GGA AAG AGC CTT GAG TGG ATT GGA GAT ATT AAT
      CTG ACC CAC TTC CTC TCT GTA CCT TTC TCG GAA CTC ACC TAA CCT CTA TAA TTA
      P   K   N   G   V   T   I   Y   N   Q   K   F   K   G   K   A   T   L
163   CCT AAA AAT GGC GTT ACT ATT TAC AAC CAG AAG TTC AAG GGC AAG GCC ACA TTG
      GGA TTT TTA CCG CAA TGA TAA ATG TTG GTC TTC CCG TTC CGG TGT AAC
      T   V   D   K   S   S   T   T   A   Y   M   E   L   R   S   L   T   S
217   ACT GTA GAC AAG TCC TCC ACC ACA GCC TAC ATG GAG CTC CGC AGC CTG ACA TCT
      TGA CAT CTG TTC AGG AGG TGG TGT CGG ATG TAC CTC GAG GCG TCG GAC TGT AGA
      E   D   T   A   V   Y   Y   C   A   R   G   D   X   Y   G   N   Y   F
271   GAA GAC ACT GCA GTC TAT TAT TGT GCA AGA GGG GAC TMC TAT GGT AAC TAC TTT
      CTT CTG TGA CGT CAG ATA ATA ACA CGT TCT CCC CTG AKC ATA CCA TTG ATG AAA
      D   Y   W   G   Q   G   T   S   L   T   V   S   S   A   K   T   T   P
325   GAC TAC TGG GGC CAA GGC ACC AGT CTC ACA GTC TCC TCA GCC AAA ACG ACM CCC
      CTG ATG ACC CCG GTT CCG TGG TCA GAG TGT CAG AGG AGT CGG TTT TGC TGK GGG
                      YOL epitope 100.0%
              ~~~~~~~~~~~~~~~~~~~~~~~~~~~~~~~
      K   L   E   E   G   E   F   S   E   A   R   V   D   I   Q   M   T   Q
379   AAG CTT GAA GAA GGT GAA TTT TCA GAA GCA CGC GTA GAC ATT CAG ATG ACA CAG
      TTC GAA CTT CTT CCA CTT AAA AGT CTT CGT GCG CAT CTG TAA GTC TAC TGT GTC
      S   P   A   S   L   S   V   S   V   G   E   T   V   T   I   T   C   R
433   TCT CCA GCC TCC CTA TCT GTA TCT GTG GGA GAA ACT GTC ACC ATC ACA TGT CGA
      AGA GGT CGG AGG GAT AGA CAT AGA CAC CCT CTT TGA CAG TGG TAG TGT ACA GCT
      T   S   E   N   I   Y   S   N   L   A   W   Y   Q   Q   K   Q   G   K
487   ACA AGT GAG AAT ATT TAC AGT AAT TTA GCA TGG TAC CAG CAG AAA CAG GGA AAA
      TGT TCA CTC TTA TAA ATG TCA TTA AAT CGT ACC ATA GTC GTC TTT GTC CCT TTT
      S   P   Q   L   L   V   Y   T   A   T   N   L   A   D   G   V   P   S
541   TCT CCT CAG CTC CTG GTC TAT ACT GCA ACA AAC TTA GCA GAT GGT GTG CCC TCA
      AGA GGA GTC GAG GAC CAG ATA TGA CGT TGT TTG AAT CGT CTA CCA CAC GGG AGT
      R   F   S   G   S   G   S   G   T   Q   Y   S   L   K   I   N   S   L
595   AGG TTC AGT GGC AGT GGA TCA GGC ACA CAG TAT TCC CTC AAG ATC AAC AGC CTG
      TCC AAG TCA CCG TCA CCT AGT CCG TGT GTC ATA AGG GAG TTC TAG TTG TCG GAC
      Q   S   D   D   S   G   T   Y   Y   C   Q   H   F   W   G   T   P   Y
649   CAG TCT GAT GAT TCT GGG ACT TAT TAC TGT CAA CAT TTT TGG GGT ACT CCG TAC
      GTC AGA CTA CTA AGA CCC TGA ATA ATG ACA GTT GTA AAA ACC CCA TGA GGC ATG
      T   F   G   G   G   T   K   L   E   I   K   R   A   D   A   A   A
703   ACG TTC GGA GGG GGG ACC AAG CTG GAA ATA AAA CGG GCT GAT GCT GCG GCC
      TGC AAG CCT CCC CCC TGG TTC GAC CTT TAT TTT GCC CGA CTA CGA CGC CGG
```

Sequence of scFv E8

Fig 13

```
      M   A   D   V   K   L   V   E   S   G   G   L   V   K   P   G   E
  1   ATG GCC GAC GTG AAG TTG GTG GAG TCT GGG GGA GGC TTA GTG AAG CCT GGA GAG
      TAC CGG CTG CAC TTC AAC CAC CTC AGA CCC CCT CCG AAT CAC TTC GGA CCT CTC
      S   L   K   L   S   C   I   A   S   G   F   T   F   S   D   Y   Y   M
 55   TCC CTG AAA CTC TCC TGT ATA GCC TCT GGA TTC ACT TTC AGT GAC TAT TAT ATG
      AGG GAC TTT GAG AGG ACA TAT CGG AGA CCT AAG TGA AAG TCA CTG ATA ATA TAC
      Y   W   V   R   Q   T   P   E   K   R   L   E   W   V   A   I   I   S
109   TAT TGG GTT CGC CAG ACT CCG GAA AAG AGG CTG GAG TGG GTC GCA ATC ATT AGT
      ATA ACC CAA GCG GTC TGA GGC CTT TTC TCC GAC CTC ACC CAG CGT TAG TAA TCA
      D   G   G   Y   Y   T   Y   Y   S   D   I   I   K   G   R   F   T   I
163   GAT GGT GGT TAT TAT ACC TAC TAT TCA GAC ATT ATC AAG GGG CGA TTC ACC ATC
      CTA CCA CCA ATA ATA TGG ATG ATA AGT CTG TAA TAG TTC CCC GCT AAG TGG TAG
      S   R   D   N   A   K   N   N   L   Y   L   Q   M   S   S   L   K   S
217   TCC AGA GAC AAT GCC AAG AAC AAC CTG TAC CTC CAA ATG AGC AGT CTG AAG TCT
      AGG TCT CTG TTA CGG TTC TTG TTG GAC ATG GAG GTT TAC TCG TCA GAC TTC AGA
      E   D   T   A   M   Y   Y   C   T   R   G   F   P   L   L   R   H   G
271   GAG GAC ACA GCC ATG TAT TAC TGT ACA AGA GGT TTT CCT CTA CTA CGG CAC GGG
      CTC CTG TGT CGG TAC ATA ATG ACA TGT TCT CCA AAA GGA GAT GAT GCC GTG CCC
      A   M   D   Y   W   G   L   G   T   S   V   T   V   S   S   T   K   T
325   GCT ATG GAC TAC TGG GGT CTT GGA ACC TCA GTC ACC GTC TCC TCA ACC AAA ACG
      CGA TAC CTG ATG ACC CCA GAA CCT TGG AGT CAG TGG CAG AGG AGT TGG TTT TGC
                              YOL epitope 100.0%
                              ~~~~~~~~~~~~~~~~~~~~~~~~~~~~~~~~~~~~~~~~
      T   P   K   L   E   E   G   E   F   S   E   A   R   V   D   I   Q   M
379   ACA CCC AAG CTT GAA GAA GGT GAA TTT TCA GAA GCA CGC GTA GAC ATT CAG ATG
      TGT GGG TTC GAA CTT CTT CCA CTT AAA AGT CTT CGT GCG CAT CTG TAA GTC TAC
      T   Q   S   P   K   F   M   S   T   S   V   G   D   R   V   S   V   T
433   ACC CAG TCT CCA AAA TTC ATG TCC ACA TCG GTA GGA GAC AGG GTC AGC GTC ACC
      TGG GTC AGA GGT TTT AAG TAC AGG TGT AGC CAT CCT CTG TCC CAG TCG CAG TGG
      C   K   A   S   Q   N   V   D   T   N   V   A   W   Y   Q   Q   K   P
487   TGC AAG GCC AGT CAG AAT GTG GAT ACT AAT GTA GCC TGG TAT CAA CAG AAA CCA
      ACG TTC CGG TCA GTC TTA CAC CTA TGA TTA CAT CGG ACC ATA GTT GTC TTT GGT
      G   Q   S   P   K   A   L   I   Y   S   A   S   Y   R   Y   S   D   V
541   GGA CAA TCT CCT AAA GCA CTG ATT TAC TCG GCA TCC TAC CGG TAC AGT GAC GTC
      CCT GTT AGA GGA TTT CGT GAC TAA ATG AGC CGT AGG ATG GCC ATG TCA CTG CAG
      P   D   R   F   T   G   S   E   S   G   T   D   F   T   L   T   I   S
595   CCT GAT CGC TTC ACA GGC AGT GAA TCT GGG ACA GAT TTC ACT CTC ACC ATC AGC
      GGA CTA GCG AAG TGT CCG TCA CTT AGA CCC TGT CTA AAG TGA GAG TGG TAG TCG
      N   V   Q   S   E   D   L   A   E   Y   F   C   Q   Q   Y   D   S   Y
649   AAT GTG CAG TCT GAA GAC TTG GCA GAG TAT TTC TGT CAG CAA TAT GAC AGC TAT
      TTA CAC GTC AGA CTT CTG AAC CGT CTC ATA AAG ACA GTC GTT ATA CTG TCG ATA
      P   Y   T   F   G   G   G   T   K   L   E   I   K   R   A   D   A   A
703   CCA TAC ACG TTC GGA GGG GGG ACC AAG CTG GAA ATA AAA CGG GCT GAT GCT GCG
      GGT ATG TGC AAG CCT CCC CCC TGG TTC GAC CTT TAT TTT GCC CGA CTA CGA CGC
      A
757   GCC
      CGG
```

Sequence of scFv A5

Fig. 14

Cytotoxic effect of recombinant immunotoxin H12-PE40 on LNCaP (black) and DU cells (white)

Construction scheme of the A5-CD3 diabody

```
     +1  M   A   R   F   S   S   S   S   L   D   L   N   W   Y   S   L   G   L   Q   X
      1  ATG GCG AGG TTC AGC TCC AGC AGT CTG GAT CTG AAC TGG TAT AGC CTG GGG CTT CAG NTG
         TAC CGC TCC AAG TCG AGG TCG TCA GAC CTA GAC TTG ACC ATA TCG GAC CCC GAA GTC NAC

CDR-H1
                                                                    ~~~~~~~~~~~~~~~~~~~
     +1  K   L   S   C   K   A   S   G   Y   T   F   T   Y   F   D   I   N   W   L   R
     61  AAA TTG TCC TGC AAG GCT TCT GGC TAC ACC TTC ACA TAC TTT GAC ATA AAC TGG TTG AGA
         TTT AAC AGG ACG TTC CGA AGA CCG ATG TGG AAG TGT ATG AAA CTG TAT TTG ACC AAC TCT

CDR-H2
                                                     ~~~~~~~~~~~~~~~~~~~~~~~~~~~~~~~~~~~
     +1  Q   R   P   E   Q   G   L   E   W   I   G   V   I   S   P   G   D   G   N   T
    121  CAG AGG CCT GAA CAG GGA CTT GAG TGG ATT GGA GTG ATT TCT CCT GGA GAT GGC AAT ACA
         GTC TCC GGA CTT GTC CCT GAA CTC ACC TAA CCT CAC TAA AGA GGA CCT CTA CCG TTA TGT

~~~~~~~~~~~~~~~~~~~~~~~~~~~~~~~~~~~~
     +1  N   Y   N   E   N   F   K   G   K   A   T   L   T   I   D   K   S   S   T   T
    181  AAC TAC AAT GAG AAC TTC AAG GGC AAG GCC ACA CTG ACT ATA GAT AAA TCC TCC ACC ACA
         TTG ATG TTA CTC TTG AAG TTC CCG TTC CGG TGT GAC TGA TAT CTA TTT AGG AGG TGG TGT

+1  A   Y   I   Q   L   S   R   L   T   S   E   D   S   A   V   Y   F   C   A   R
    241  GCC TAC ATT CAG CTT AGC AGG CTG ACA TCT GAG GAC TCT GCT GTC TAT TTC TGT GCA AGA
         CGG ATG TAA GTC GAA TCG TCC GAC TGT AGA CTC CTG AGA CGA CAG ATA AAG ACA CGT TCT

CDR-H3
         ~~~~~~~~~~~~~~~~~~~~~~~~~~~~~~~~~~~~~~~~~~~~~~~~
     +1  D   G   N   F   P   Y   Y   A   M   D   S   W   G   Q   G   T   S   V   T   V
    301  GAT GGC AAC TTC CCT TAC TAT GCT ATG GAC TCA TGG GGT CAA GGA ACC TCA GTC ACC GTC
         CTA CCG TTG AAG GGA ATG ATA CGA TAC CTG AGT ACC CCA GTT CCT TGG AGT CAG TGG CAG

YOL-epitope
                                 ~~~~~~~~~~~~~~~~~~~~~~~~~~~~~~~~~~~~~
     +1  S   S   A   K   T   T   P   K   L   E   E   G   E   F   S   E   A   R   V   D
    361  TCC TCA GCC AAA ACG ACA CCC AAG CTT GAA GAA GGT GAA TTT TCA GAA GCA CGC GTA GAC
         AGG AGT CGG TTT TGC TGT GGG TTC GAA CTT CTT CCA CTT AAA AGT CTT CGT GCG CAT CTG +1  I   V   M   T   Q   I   P   L   S   L   P   V   I   L   G   D   Q   A   S   I
    421  ATT GTG ATG ACC CAG ATT CCA CTC TCC CTG CCT GTC ATT CTT GGA GAT CAA GCC TCC ATC
         TAA CAC TAC TGG GTC TAA GGT GAG AGG GAC GGA CAG TAA GAA CCT CTA GTT CGG AGG TAG CDR-L1
             ~~~~~~~~~~~~~~~~~~~~~~~~~~~~~~~~~~~~~~~~~~~~~~~~~~~~~~~~~~~~~~
     +1  S   C   R   S   S   Q   S   L   V   Y   S   N   G   N   T   Y   L   H   W   F
    481  TCT TGC AGA TCT AGT CAG AGC CTT GTA TAC AGT AAT GGA AAC ACC TAT TTA CAT TGG TTC
         AGA ACG TCT AGA TCA GTC TCG GAA CAT ATG TCA TTA CCT TTG TGG ATA AAT GTA ACC AAG CDR-L2
                                                            ~~~~~~~~~~~~~~~~~~~~~~~~~~~
     +1  L   Q   K   P   G   Q   S   P   K   L   L   I   Y   N   V   S   N   L   F   S
    541  CTG CAG AAG CCA GGC CAG TCT CCA AAG CTC CTG ATC TAC AAT GTT TCC AAC CTA TTT TCT
         GAC GTC TTC GGT CCG GTC AGA GGT TTC GAG GAC TAG ATG TTA CAA AGG TTG GAT AAA AGA Fig. 20 a
     +1  G   V   P   D   R   F   S   G   S   G   S   G   T   D   F   T   L   K   I   S
    601  GGG GTC CCA GAC AGG TTC AGT GGC AGT GGA TCA GGG ACT GAT TTC ACA CTC AAG ATC AGC
         CCC CAG GGT CTG TCC AAG TCA CCG TCA CCT AGT CCC TGA CTA AAG TGT GAG TTC TAG TCG
```

```
                                                      CDR-L3
                                                      ~~~~~~~~~~~~~~~~~~~~~~~~~~~~~~~
   +1  R   V   E   A   E   D   L   G   I   Y   F   C   S   Q   S   T   H   V   P   T
  661 AGA GTG GAG GCT GAG GAT CTG GGA ATT TAT TTC TGC TCT CAA AGT ACA CAT GTT CCC ACG
      TCT CAC CTC CGA CTC CTA GAC CCT TAA ATA AAG ACG AGA GTT TCA TGT GTA CAA GGG TGC

+1  F   G   G   G   T   K   L   E   I   K   R   A   D   A   A   A   A   G   S
  721 TTC GGA GGG GGG ACC AAG CTG GAA ATA AAA CGG GCT GAT GCT GCG GCC GCT GGA TCC
      AAG CCT CCC CCC TGG TTC GAC CTT TAT TTT GCC CGA CTA CGA CGC CGG CGA CCT AGG
```

Sequence of scFv H12

Fig. 20 b

```
         M   A   Q   V   Q   L   Q   Q   S   G   A   E   L   V   E   P   G   A   S   V
   1   ATG GCC CAG GTG CAG CTG CAG CAG TCT GGG GCT GAA CTG GTA GAG CCT GGG GCT TCA GTG
       TAC CGG GTC CAC GTC GAC GTC GTC AGA CCC CGA CTT GAC CAT CTC GGA CCC CGA AGT CAC

CDR-H1
                                                         ~~~~~~~~~~~~~~~~~~~
  +1   K   L   S   C   K   A   S   G   Y   T   F   T   Y   F   D   I   N   W   L   R
  61   AAA CTG TCC TGC AAG GCT TCT GGC TAC ACC TTC ACA TAC TTT GAC ATA AAC TGG TTG AGA
       TTT GAC AGG ACG TTC CGA AGA CCG ATG TGG AAG TGT ATG AAA CTG TAT TTG ACC AAC TCT

CDR-H2
                                             ~~~~~~~~~~~~~~~~~~~~~~~~~~~~~~~~~~~~~
  +1   Q   R   P   E   Q   G   L   E   W   I   G   G   I   S   P   G   D   G   N   T
 121   CAG AGG CCT GAA CAG GGA CTT GAG TGG ATT GGA GGG ATT TCT CCT GGA GAT GGT AAT ACA
       GTC TCC GGA CTT GTC CCT GAA CTC ACC TAA CCT CCC TAA AGA GGA CCT CTA CCA TTA TGT

~~~~~~~~~~~~~~~~~~~~~~~~~~~~~~~~
  +1   N   Y   N   E   N   F   K   G   K   A   L   T   I   D   K   S   S   T   T
 181   AAC TAC AAT GAG AAC TTC AAG GGC AAG GCC ACA CTG ACT ATA GAC AAA TCC TCC ACC ACA
       TTG ATG TTA CTC TTG AAG TTC CCG TTC CGG TGT GAC TGA TAT CTG TTT AGG AGG TGG TGT

+1   A   Y   I   Q   L   S   R   L   T   S   E   D   S   A   V   Y   F   C   A   R
 241   GCC TAC ATT CAG CTC AGC AGG CTG ACA TCT GAG GAC TCT GCT GTC TAT TTC TGT GCA AGA
       CGG ATG TAA GTC GAG TCG TCC GAC TGT AGA CTC CTG AGA CGA CAG ATA AAG ACA CGT TCT

CDR H3
       ~~~~~~~~~~~~~~~~~~~~~~~~~~~~~~~~~~~~~~~~~~~~~~~~~~
  +1   D   G   N   F   P   Y   Y   A   M   D   S   W   G   Q   G   T   S   V   T   V
 301   GAT GGC AAC TTC CCT TAC TAT GCT ATG GAC TCA TGG GGT CAA GGA ACC TCA GTC ACC GTC
       CTA CCG TTG AAG GGA ATG ATA CGA TAC CTG AGT ACC CCA GTT CCT TGG AGT CAG TGG CAG

YOL-epitope
                                     ~~~~~~~~~~~~~~~~~~~~~~~~~~~~~
  +1   S   S   A   K   T   T   P   K   L   E   E   G   E   F   S   E   A   R   V   D
 361   TCC TCA GCC AAA ACG ACA CCC AAG CTT GAA GAA GGT GAA TTT TCA GAA GCA CGC GTA GAC
       AGG AGT CGG TTT TGC TGT GGG TTC GAA CTT CTT CCA CTT AAA AGT CTT CGT GCG CAT CTG +1   I   E   L   T   Q   S   P   L   S   L   P   V   I   L   G   D   Q   A   S   I
 421   ATT GAG CTC ACC CAA TCT CCA CTC TCC CTG CCT GTC ATT CTT GGA GAT CAA GCC TCC ATC
       TAA CTC GAG TGG GTT AGA GGT GAG AGG GAC GGA CAG TAA GAA CCT CTA GTT CGG AGG TAG CDR-L1
       ~~~~~~~~~~~~~~~~~~~~~~~~~~~~~~~~~~~~~~~~~~~~~~~~~~~~~~~~
  +1   S   C   R   S   S   Q   S   L   V   H   S   N   G   N   T   Y   L   H   W   F
 481   TCT TGC AGA TCT AGT CAG AGC CTT GTA CAC AGT AAT GGA AAC ACC TAT TTA CAT TGG TTT
       AGA ACG TCT AGA TCA GTC TCG GAA CAT GTG TCA TTA CCT TTG TGG ATA AAT GTA ACC AAA CDR-L2
                                                     ~~~~~~~~~~~~~~~~~~~~~~~~~~~
  +1   L   Q   K   P   G   Q   S   P   K   L   L   I   Y   T   V   S   N   R   F   S
 541   CTG CAG AAG CCA GGC CAG TCT CCA AAG CTC CTG ATC TAC ACA GTT TCC AAC CGA TTT TCT
       GAC GTC TTC GGT CCG GTC AGA GGT TTC GAG GAC TAG ATG TGT CAA AGG TTG GCT AAA AGA Fig. 21 a
  +1   G   V   P   D   R   F   S   G   S   G   S   G   T   D   F   T   L   K   I   S
 601   GGG GTC CCA GAC AGG TTC AGT GGC AGT GGA TCA GGG ACA GAT TTC ACA CTC AAG ATC AGC
       CCC CAG GGT CTG TCC AAG TCA CCG TCA CCT AGT CCC TGT CTA AAG TGT GAG TTC TAG TCG
```

```
                                                                CDR-L3
                                                          ~~~~~~~~~~~~~~~~~~~~~~~~~~~~~~
     +1   R   V   E   A   E   D   L   G   V   Y   F   C   S   Q   S   T   H   V   P   T
    661  AGA GTG GAG GCT GAG GAT CTG GGA GTT TAT TTC TGC TCT CAA AGT ACC CAT GTT CCC ACG
         TCT CAC CTC CGA CTC CTA GAC CCT CAA ATA AAG ACG AGA GTT TCA TGG GTA CAA GGG TGC

+1   F   G   G   G   T   K   L   E   I   K   R   A   D   A   A   A   G   S
    721  TTC GGA GGG GGG ACC AAG CTG GAA ATA AAA CGG GCT GAT GCT GCG GCC GCT GGA TCC
         AAG CCT CCC CCC TGG TTC GAC CTT TAT TTT GCC CGA CTA CGA CGC CGG CGA CCT AGG

Sequence of scFv D7
```

Fig. 21 b

SEQUENCE LISTING

```
<160> NUMBER OF SEQ ID NOS: 33

<210> SEQ ID NO 1
<211> LENGTH: 251
<212> TYPE: PRT
<213> ORGANISM: Artificial
<220> FEATURE:
<223> OTHER INFORMATION: scFv E8
<220> FEATURE:
<221> NAME/KEY: MISC_FEATURE
<222> LOCATION: (103)..(103)
<223> OTHER INFORMATION: Xaa means Tyr or Ser

<400> SEQUENCE: 1

Met Ala Glu Val Gln Leu Gln Gln Ser Gly Pro Asp Leu Val Lys Pro
1               5                   10                  15

Gly Ala Ser Met Lys Ile Ser Cys Lys Ala Ser Gly Tyr Thr Phe Thr
            20                  25                  30

Asp Tyr Asn Met Asp Trp Val Lys Glu Arg His Gly Lys Ser Leu Glu
        35                  40                  45

Trp Ile Gly Asp Ile Asn Pro Lys Asn Gly Val Thr Ile Tyr Asn Gln
    50                  55                  60

Lys Phe Lys Gly Lys Ala Thr Leu Thr Val Asp Lys Ser Ser Thr Thr
65                  70                  75                  80

Ala Tyr Met Glu Leu Arg Ser Leu Thr Ser Glu Asp Thr Ala Val Tyr
                85                  90                  95

Tyr Cys Ala Arg Gly Asp Xaa Tyr Gly Asn Tyr Phe Asp Tyr Trp Gly
            100                 105                 110

Gln Gly Thr Ser Leu Thr Val Ser Ser Ala Lys Thr Thr Pro Lys Leu
        115                 120                 125

Glu Glu Gly Glu Phe Ser Glu Ala Arg Val Asp Ile Gln Met Thr Gln
    130                 135                 140

Ser Pro Ala Ser Leu Ser Val Ser Val Gly Glu Thr Val Thr Ile Thr
145                 150                 155                 160

Cys Arg Thr Ser Glu Asn Ile Tyr Ser Asn Leu Ala Trp Tyr Gln Gln
                165                 170                 175

Lys Gln Gly Lys Ser Pro Gln Leu Leu Val Tyr Thr Ala Thr Asn Leu
            180                 185                 190

Ala Asp Gly Val Pro Ser Arg Phe Ser Gly Ser Gly Ser Gly Thr Gln
        195                 200                 205

Tyr Ser Leu Lys Ile Asn Ser Leu Gln Ser Asp Asp Ser Gly Thr Tyr
    210                 215                 220

Tyr Cys Gln His Phe Trp Gly Thr Pro Tyr Thr Phe Gly Gly Gly Thr
225                 230                 235                 240

Lys Leu Glu Ile Lys Arg Ala Asp Ala Ala Ala
```

```
                245                 250
```

<210> SEQ ID NO 2
<211> LENGTH: 10
<212> TYPE: PRT
<213> ORGANISM: Artificial
<220> FEATURE:
<223> OTHER INFORMATION: CDR sequence

<400> SEQUENCE: 2

```
Gly Tyr Thr Phe Thr Asp Tyr Asn Met Asp
1               5                   10
```

<210> SEQ ID NO 3
<211> LENGTH: 11
<212> TYPE: PRT
<213> ORGANISM: Artificial
<220> FEATURE:
<223> OTHER INFORMATION: CDR sequence

<400> SEQUENCE: 3

```
Gly Asp Ile Asn Pro Lys Asn Gly Val Thr Ile
1               5                   10
```

<210> SEQ ID NO 4
<211> LENGTH: 11
<212> TYPE: PRT
<213> ORGANISM: Artificial
<220> FEATURE:
<223> OTHER INFORMATION: CDR sequence
<220> FEATURE:
<221> NAME/KEY: MISC_FEATURE
<222> LOCATION: (4)..(4)
<223> OTHER INFORMATION: Xaa means Tyr or Ser

<400> SEQUENCE: 4

```
Arg Gly Asp Xaa Tyr Gly Asn Tyr Phe Asp Tyr
1               5                   10
```

<210> SEQ ID NO 5
<211> LENGTH: 11
<212> TYPE: PRT
<213> ORGANISM: Artificial
<220> FEATURE:
<223> OTHER INFORMATION: CDR sequence

<400> SEQUENCE: 5

```
Arg Thr Ser Glu Asn Ile Tyr Ser Asn Leu Ala
1               5                   10
```

<210> SEQ ID NO 6
<211> LENGTH: 7
<212> TYPE: PRT
<213> ORGANISM: Artificial
<220> FEATURE:
<223> OTHER INFORMATION: CDR sequence

<400> SEQUENCE: 6

```
Thr Ala Thr Asn Leu Ala Asp
1               5
```

<210> SEQ ID NO 7
<211> LENGTH: 9
<212> TYPE: PRT
<213> ORGANISM: Artificial
<220> FEATURE:
<223> OTHER INFORMATION: CDR sequence

<400> SEQUENCE: 7

```
Gln His Phe Trp Gly Thr Pro Tyr Thr
1               5
```

<210> SEQ ID NO 8
<211> LENGTH: 753
<212> TYPE: DNA
<213> ORGANISM: Artificial
<220> FEATURE:
<223> OTHER INFORMATION: scFv E8

<400> SEQUENCE: 8

| | | | | | |
|---|---|---|---|---|---|
| atggccgagg | tgcagctgca | gcagtcagga | cccgacctgg | tgaagcctgg | ggcctcaatg | 60 |
| aagatttcct | gcaaggcttc | tggatacaca | ttcactgact | acaacatgga | ctgggtgaag | 120 |
| gagagacatg | aaagagcct | tgagtggatt | ggagatatta | tcctaaaaa | tggcgttact | 180 |
| atttacaacc | agaagttcaa | gggcaaggcc | acattgactg | tagacaagtc | ctccaccaca | 240 |
| gcctacatgg | agctccgcag | cctgacatct | gaagacactg | cagtctatta | ttgtgcaaga | 300 |
| ggggactmct | atggtaacta | ctttgactac | tggggccaag | gcaccagtct | cacagtctcc | 360 |
| tcagccaaaa | cgacmcccaa | gcttgaagaa | ggtgaatttt | cagaagcacg | cgtagacatt | 420 |
| cagatgacac | agtctccagc | ctccctatct | gtatctgtgg | gagaaactgt | caccatcaca | 480 |
| tgtcgaacaa | gtgagaatat | ttacagtaat | ttagcatggt | atcagcagaa | acagggaaaa | 540 |
| tctcctcagc | tcctggtcta | tactgcaaca | aacttagcag | atggtgtgcc | ctcaaggttc | 600 |
| agtggcagtg | gatcaggcac | acagtattcc | ctcaagatca | acagcctgca | gtctgatgat | 660 |
| tctgggactt | attactgtca | acatttttgg | ggtactccgt | acacgttcgg | aggggggacc | 720 |
| aagctggaaa | taaacgggc | tgatgctgcg | gcc | | | 753 |

<210> SEQ ID NO 9
<211> LENGTH: 753
<212> TYPE: DNA
<213> ORGANISM: Artificial
<220> FEATURE:
<223> OTHER INFORMATION: reverse and complement of SEQ ID NO:8

<400> SEQUENCE: 9

| | | | | | |
|---|---|---|---|---|---|
| ggccgcagca | tcagcccgtt | ttatttccag | cttggtcccc | cctccgaacg | tgtacggagt | 60 |
| accccaaaaa | tgttgacagt | aataagtccc | agaatcatca | gactgcaggc | tgttgatctt | 120 |
| gagggaatac | tgtgtgcctg | atccactgcc | actgaacctt | gagggcacac | catctgctaa | 180 |
| gtttgttgca | gtatagacca | ggagctgagg | agatttccc | tgtttctgct | gataccatgc | 240 |
| taaattactg | taaatattct | cacttgttcg | acatgtgatg | gtgacagttt | ctcccacaga | 300 |
| tacagatagg | gaggctggag | actgtgtcat | ctgaatgtct | acgcgtgctt | ctgaaaattc | 360 |
| accttcttca | agcttgggkg | tcgttttggc | tgaggagact | gtgagactgg | tgccttggcc | 420 |
| ccagtagtca | aagtagttac | catagkagtc | ccctcttgca | caataataga | ctgcagtgtc | 480 |
| ttcagatgtc | aggctgcgga | gctccatgta | ggctgtggtg | gaggacttgt | ctacagtcaa | 540 |
| tgtggccttg | cccttgaact | tctggttgta | aatagtaacg | ccatttttag | gattaatatc | 600 |
| tccaatccac | tcaaggctct | ttccatgtct | ctccttcacc | cagtccatgt | tgtagtcagt | 660 |
| gaatgtgtat | ccagaagcct | tgcaggaaat | cttcattgag | gccccaggct | tcaccaggtc | 720 |
| gggtcctgac | tgctgcagct | gcacctcggc | cat | | | 753 |

<210> SEQ ID NO 10
<211> LENGTH: 253
<212> TYPE: PRT

```
<213> ORGANISM: Artificial
<220> FEATURE:
<223> OTHER INFORMATION: scFv A5

<400> SEQUENCE: 10

Met Ala Asp Val Lys Leu Val Glu Ser Gly Gly Gly Leu Val Lys Pro
1               5                   10                  15

Gly Glu Ser Leu Lys Leu Ser Cys Ile Ala Ser Gly Phe Thr Phe Ser
            20                  25                  30

Asp Tyr Tyr Met Tyr Trp Val Arg Gln Thr Pro Glu Lys Arg Leu Glu
        35                  40                  45

Trp Val Ala Ile Ile Ser Asp Gly Gly Tyr Tyr Thr Tyr Tyr Ser Asp
    50                  55                  60

Ile Ile Lys Gly Arg Phe Thr Ile Ser Arg Asp Asn Ala Lys Asn Asn
65                  70                  75                  80

Leu Tyr Leu Gln Met Ser Ser Leu Lys Ser Glu Asp Thr Ala Met Tyr
                85                  90                  95

Tyr Cys Thr Arg Gly Phe Pro Leu Leu Arg His Gly Ala Met Asp Tyr
            100                 105                 110

Trp Gly Leu Gly Thr Ser Val Thr Val Ser Ser Thr Lys Thr Thr Pro
            115                 120                 125

Lys Leu Glu Glu Gly Glu Phe Ser Glu Ala Arg Val Asp Ile Gln Met
130                 135                 140

Thr Gln Ser Pro Lys Phe Met Ser Thr Ser Val Gly Asp Arg Val Ser
145                 150                 155                 160

Val Thr Cys Lys Ala Ser Gln Asn Val Asp Thr Asn Val Ala Trp Tyr
            165                 170                 175

Gln Gln Lys Pro Gly Gln Ser Pro Lys Ala Leu Ile Tyr Ser Ala Ser
            180                 185                 190

Tyr Arg Tyr Ser Asp Val Pro Asp Arg Phe Thr Gly Ser Glu Ser Gly
            195                 200                 205

Thr Asp Phe Thr Leu Thr Ile Ser Asn Val Gln Ser Glu Asp Leu Ala
            210                 215                 220

Glu Tyr Phe Cys Gln Gln Tyr Asp Ser Tyr Pro Tyr Thr Phe Gly Gly
225                 230                 235                 240

Gly Thr Lys Leu Glu Ile Lys Arg Ala Asp Ala Ala Ala
                245                 250

<210> SEQ ID NO 11
<211> LENGTH: 9
<212> TYPE: PRT
<213> ORGANISM: Artificial
<220> FEATURE:
<223> OTHER INFORMATION: CDR sequence

<400> SEQUENCE: 11

Gly Phe Thr Phe Ser Asp Tyr Tyr Met
1               5

<210> SEQ ID NO 12
<211> LENGTH: 7
<212> TYPE: PRT
<213> ORGANISM: Artificial
<220> FEATURE:
<223> OTHER INFORMATION: CDR sequence

<400> SEQUENCE: 12

Ile Ile Ser Asp Gly Gly Tyr
1               5
```

```
<210> SEQ ID NO 13
<211> LENGTH: 12
<212> TYPE: PRT
<213> ORGANISM: Artificial
<220> FEATURE:
<223> OTHER INFORMATION: CDR sequence

<400> SEQUENCE: 13

Gly Phe Pro Leu Leu Arg His Gly Ala Met Asp Tyr
1               5                   10

<210> SEQ ID NO 14
<211> LENGTH: 11
<212> TYPE: PRT
<213> ORGANISM: Artificial
<220> FEATURE:
<223> OTHER INFORMATION: CDR sequence

<400> SEQUENCE: 14

Lys Ala Ser Gln Asn Val Asp Thr Asn Val Ala
1               5                   10

<210> SEQ ID NO 15
<211> LENGTH: 7
<212> TYPE: PRT
<213> ORGANISM: Artificial
<220> FEATURE:
<223> OTHER INFORMATION: CDR sequence

<400> SEQUENCE: 15

Ser Ala Ser Tyr Arg Tyr Ser
1               5

<210> SEQ ID NO 16
<211> LENGTH: 9
<212> TYPE: PRT
<213> ORGANISM: Artificial
<220> FEATURE:
<223> OTHER INFORMATION: CDR sequence

<400> SEQUENCE: 16

Gln Gln Tyr Asp Ser Tyr Pro Tyr Thr
1               5

<210> SEQ ID NO 17
<211> LENGTH: 759
<212> TYPE: DNA
<213> ORGANISM: Artificial
<220> FEATURE:
<223> OTHER INFORMATION: scFv A5

<400> SEQUENCE: 17
atggccgacg tgaagttggt ggagtctggg ggaggcttag tgaagcctgg agagtccctg     60
aaactctcct gtatagcctc tggattcact ttcagtgact attatatgta ttggttcgc    120 cagactccgg aaaagaggct ggagtgggtc gcaatcatta gtgatggtgg ttattatacc    180
tactattcag acattatcaa ggggcgattc accatctcca gagacaatgc caagaacaac    240
ctgtacctcc aaatgagcag tctgaagtct gaggacacag ccatgtatta ctgtacaaga    300
ggttttcctc tactacggca cggggctatg gactactggg gtcttggaac ctcagtcacc    360
gtctcctcaa ccaaaacgac acccaagctt gaagaaggtg aattttcaga agcacgcgta    420
gacattcaga tgacccagtc tccaaaattc atgtccacat cggtaggaga cagggtcagc    480
gtcacctgca aggccagtca gaatgtggat actaatgtag cctggtatca acagaaacca    540
```

```
ggacaatctc ctaaagcact gatttactcg gcatcctacc ggtacagtga cgtccctgat    600
cgcttcacag gcagtgaatc tgggacagat ttcactctca ccatcagcaa tgtgcagtct    660
gaagacttgg cagagtattt ctgtcagcaa tatgacagct atccatacac gttcggaggg    720
gggaccaagc tggaaataaa acgggctgat gctgcggcc                           759
```

<210> SEQ ID NO 18
<211> LENGTH: 759
<212> TYPE: DNA
<213> ORGANISM: Artificial
<220> FEATURE:
<223> OTHER INFORMATION: reverse and complement of SEQ ID NO:17

<400> SEQUENCE: 18

```
ggccgcagca tcagcccgtt ttatttccag cttggtcccc cctccgaacg tgtatggata     60
gctgtcatat tgctgacaga atactctgcc aagtcttca gactgcacat tgctgatggt    120
gagagtgaaa tctgtcccag attcactgcc tgtgaagcga tcagggacgt cactgtaccg    180
gtaggatgcc gagtaaatca gtgctttagg agattgtcct ggtttctgtt gataccaggc    240
tacattagta tccacattct gactggcctt gcaggtgacg ctgaccctgt ctcctaccga    300
tgtggacatg aattttggag actgggtcat ctgaatgtct acgcgtgctt ctgaaaattc    360
accttcttca gcttgggtg tcgttttggt tgaggagacg gtgactgagg ttccaagacc    420
ccagtagtcc atagccccgt gccgtagtag aggaaaacct cttgtacagt aatacatggc    480
tgtgtcctca gacttcagac tgctcatttg gaggtacagg ttgttcttgg cattgtctct    540
ggagatggtg aatcgcccct tgataatgtc tgaatagtag gtataataac caccatcact    600
aatgattgcg acccactcca gcctcttttc cggagtctgg cgaacccaat acatataata    660
gtcactgaaa gtgaatccag aggctataca ggagagtttc agggactctc caggcttcac    720
taagcctccc ccagactcca ccaacttcac gtcggccat                           759
```

<210> SEQ ID NO 19
<211> LENGTH: 777
<212> TYPE: DNA
<213> ORGANISM: artificial
<220> FEATURE:
<223> OTHER INFORMATION: scFv H12
<220> FEATURE:
<221> NAME/KEY: misc_feature
<222> LOCATION: (58)..(58)
<223> OTHER INFORMATION: n is a, c, g, or t

<400> SEQUENCE: 19

```
atggcgaggt tcagctccag cagtctggat ctgaactggt atagcctggg gcttcagntg     60
aaattgtcct gcaaggcttc tggctacacc ttcacatact ttgacataaa ctggttgaga    120
cagaggcctg aacagggact tgagtggatt ggagtgattt ctcctggaga tggcaataca    180
aactacaatg agaacttcaa gggcaaggcc acactgacta tagataaatc ctccaccaca    240
gcctacattc agcttagcag gctgacatct gaggactctg ctgtctattt ctgtgcaaga    300
gatggcaact tcccttacta tgctatggac tcatggggtc aaggaacctc agtcaccgtc    360
tcctcagcca aaacgacacc caagcttgaa gaaggtgaat tttcagaagc acgcgtagac    420
attgtgatga cccagattcc actctccctg cctgtcattc ttggagatca agcctccatc    480
tcttgcagat ctagtcagag ccttgtatac agtaatggaa acacctattt acattggttc    540
ctgcagaagc caggccagtc tccaaagctc ctgatctaca tgtttccaa cctatttct    600 ggggtcccag acaggttcag tggcagtgga tcagggactg atttcacact caagatcagc    660
```

```
agagtggagg ctgaggatct gggaatttat ttctgctctc aaagtacaca tgttcccacg    720
ttcggagggg ggaccaagct ggaaataaaa cgggctgatg ctgcggccgc tggatcc       777
```

<210> SEQ ID NO 20
<211> LENGTH: 259
<212> TYPE: PRT
<213> ORGANISM: artificial
<220> FEATURE:
<223> OTHER INFORMATION: scFv H12
<220> FEATURE:
<221> NAME/KEY: MISC_FEATURE
<222> LOCATION: (20)..(20)
<223> OTHER INFORMATION: The 'Xaa' at location 20 stands for Met, Val,
      or Leu.

<400> SEQUENCE: 20

```
Met Ala Arg Phe Ser Ser Ser Leu Asp Leu Asn Trp Tyr Ser Leu
1               5                   10                  15

Gly Leu Gln Xaa Lys Leu Ser Cys Lys Ala Ser Gly Tyr Thr Phe Thr
            20                  25                  30

Tyr Phe Asp Ile Asn Trp Leu Arg Gln Arg Pro Glu Gln Gly Leu Glu
        35                  40                  45

Trp Ile Gly Val Ile Ser Pro Gly Asp Gly Asn Thr Asn Tyr Asn Glu
50                  55                  60

Asn Phe Lys Gly Lys Ala Thr Leu Thr Ile Asp Lys Ser Ser Thr Thr
65                  70                  75                  80

Ala Tyr Ile Gln Leu Ser Arg Leu Thr Ser Glu Asp Ser Ala Val Tyr
                85                  90                  95

Phe Cys Ala Arg Asp Gly Asn Phe Pro Tyr Tyr Ala Met Asp Ser Trp
            100                 105                 110

Gly Gln Gly Thr Ser Val Thr Val Ser Ser Ala Lys Thr Thr Pro Lys
        115                 120                 125

Leu Glu Glu Gly Glu Phe Ser Glu Ala Arg Val Asp Ile Val Met Thr
    130                 135                 140

Gln Ile Pro Leu Ser Leu Pro Val Ile Leu Gly Asp Gln Ala Ser Ile
145                 150                 155                 160

Ser Cys Arg Ser Ser Gln Ser Leu Val Tyr Ser Asn Gly Asn Thr Tyr
                165                 170                 175

Leu His Trp Phe Leu Gln Lys Pro Gly Gln Ser Pro Lys Leu Leu Ile
            180                 185                 190

Tyr Asn Val Ser Asn Leu Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Leu Gly Ile Tyr Phe Cys Ser Gln Ser Thr His Val Pro Thr
225                 230                 235                 240

Phe Gly Gly Gly Thr Lys Leu Glu Ile Lys Arg Ala Asp Ala Ala Ala
                245                 250                 255

Ala Gly Ser
```

<210> SEQ ID NO 21
<211> LENGTH: 777
<212> TYPE: DNA
<213> ORGANISM: artificial
<220> FEATURE:
<223> OTHER INFORMATION: scFv D7

<400> SEQUENCE: 21

```
atggcccagg tgcagctgca gcagtctggg gctgaactgg tagagcctgg ggcttcagtg    60
```

```
aaactgtcct gcaaggcttc tggctacacc ttcacatact ttgacataaa ctggttgaga      120
cagaggcctg aacagggact tgagtggatt ggagggattt ctcctggaga tggtaataca      180
aactacaatg agaacttcaa gggcaaggcc acactgacta tagacaaatc ctccaccaca      240
gcctacattc agctcagcag gctgacatct gaggactctg ctgtctattt ctgtgcaaga      300
gatggcaact cccttactat gctatggac tcatggggtc aaggaacctc agtcaccgtc        360
tcctcagcca aaacgacacc caagcttgaa gaaggtgaat tttcagaagc acgcgtagac      420
attgagctca cccaatctcc actctccctg cctgtcattc ttggagatca agcctccatc      480
tcttgcagat ctagtcagag ccttgtacac agtaatggaa acacctattt acattggttt      540
ctgcagaagc caggccagtc tccaaagctc ctgatctaca gtttccaa ccgattttct          600 ggggtcccag acaggttcag tggcagtgga tcagggacag atttcacact caagatcagc      660
agagtggagg ctgaggatct gggagtttat ttctgctctc aaagtaccca tgttcccacg      720
ttcgaggggg ggaccaagct ggaaataaaa cgggctgatg ctgcggccgc tggatcc        777
```

<210> SEQ ID NO 22
<211> LENGTH: 259
<212> TYPE: PRT
<213> ORGANISM: artificial
<220> FEATURE:
<223> OTHER INFORMATION: scFv D7

<400> SEQUENCE: 22

```
Met Ala Gln Val Gln Leu Gln Gln Ser Gly Ala Glu Leu Val Glu Pro
1               5                   10                  15

Gly Ala Ser Val Lys Leu Ser Cys Lys Ala Ser Gly Tyr Thr Phe Thr
            20                  25                  30

Tyr Phe Asp Ile Asn Trp Leu Arg Gln Arg Pro Glu Gln Gly Leu Glu
        35                  40                  45

Trp Ile Gly Gly Ile Ser Pro Gly Asp Gly Asn Thr Asn Tyr Asn Glu
    50                  55                  60

Asn Phe Lys Gly Lys Ala Thr Leu Thr Ile Asp Lys Ser Ser Thr Thr
65                  70                  75                  80

Ala Tyr Ile Gln Leu Ser Arg Leu Thr Ser Glu Asp Ser Ala Val Tyr
                85                  90                  95

Phe Cys Ala Arg Asp Gly Asn Phe Pro Tyr Tyr Ala Met Asp Ser Trp
            100                 105                 110

Gly Gln Gly Thr Ser Val Thr Val Ser Ser Ala Lys Thr Thr Pro Lys
        115                 120                 125

Leu Glu Glu Gly Glu Phe Ser Glu Ala Arg Val Asp Ile Glu Leu Thr
    130                 135                 140

Gln Ser Pro Leu Ser Leu Pro Val Ile Leu Gly Asp Gln Ala Ser Ile
145                 150                 155                 160

Ser Cys Arg Ser Ser Gln Ser Leu Val His Ser Asn Gly Asn Thr Tyr
                165                 170                 175

Leu His Trp Phe Leu Gln Lys Pro Gly Gln Ser Pro Lys Leu Leu Ile
            180                 185                 190

Tyr Thr Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Leu Gly Val Tyr Phe Cys Ser Gln Ser Thr His Val Pro Thr
225                 230                 235                 240
```

-continued

Phe Gly Gly Gly Thr Lys Leu Glu Ile Lys Arg Ala Asp Ala Ala Ala
                245                 250                 255

Ala Gly Ser

<210> SEQ ID NO 23
<211> LENGTH: 777
<212> TYPE: DNA
<213> ORGANISM: artificial
<220> FEATURE:
<223> OTHER INFORMATION: scFv H12-reverse and complement of SEQ ID NO:19
<220> FEATURE:
<221> NAME/KEY: misc_feature
<222> LOCATION: (720)..(720)
<223> OTHER INFORMATION: n is a, c, g, or t

<400> SEQUENCE: 23

```
ggatccagcg gccgcagcat cagcccgttt tatttccagc ttggtccccc ctccgaacgt    60
gggaacatgt gtactttgag agcagaaata aattcccaga tcctcagcct ccactctgct   120
gatcttgagt gtgaaatcag tccctgatcc actgccactg aacctgtctg gaccccaga   180
aaataggttg gaaacattgt agatcaggag ctttggagac tggcctggct tctgcaggaa   240
ccaatgtaaa taggtgtttc cattactgta tacaaggctc tgactagatc tgcaagagat   300
ggaggcttga tctccaagaa tgacaggcag ggagagtgga atctgggtca tcacaatgtc   360
tacgcgtgct tctgaaaatt caccttcttc aagcttgggt gtcgttttgg ctgaggagac   420
ggtgactgag gttccttgac cccatgagtc catagcatag taagggaagt tgccatctct   480
tgcacagaaa tagacagcag agtcctcaga tgtcagcctg ctaagctgaa tgtaggctgt   540
ggtggaggat ttatctatag tcagtgtggc cttgcccttg aagttctcat tgtagtttgt   600
attgccatct ccaggagaaa tcactccaat ccactcaagt ccctgttcag gcctctgtct   660
caaccagttt atgtcaaagt atgtgaaggt gtagccagaa gccttgcagg acaatttcan   720
ctgaagcccc aggctatacc agttcagatc cagactgctg gagctgaacc tcgccat     777
```

<210> SEQ ID NO 24
<211> LENGTH: 777
<212> TYPE: DNA
<213> ORGANISM: artificial
<220> FEATURE:
<223> OTHER INFORMATION: scFv D7 reverse and complement of SEQ ID NO:21

<400> SEQUENCE: 24

```
ggatccagcg gccgcagcat cagcccgttt tatttccagc ttggtccccc ctccgaacgt    60
gggaacatgg gtactttgag agcagaaata aactcccaga tcctcagcct ccactctgct   120
gatcttgagt gtgaaatctg tccctgatcc actgccactg aacctgtctg gaccccaga   180
aaatcggttg gaaactgtgt agatcaggag ctttggagac tggcctggct tctgcagaaa   240
ccaatgtaaa taggtgtttc cattactgtg tacaaggctc tgactagatc tgcaagagat   300
ggaggcttga tctccaagaa tgacaggcag ggagagtgga gattgggtga gctcaatgtc   360
tacgcgtgct tctgaaaatt caccttcttc aagcttgggt gtcgttttgg ctgaggagac   420
ggtgactgag gttccttgac cccatgagtc catagcatag taagggaagt tgccatctct   480
tgcacagaaa tagacagcag agtcctcaga tgtcagcctg ctgagctgaa tgtaggctgt   540
ggtggaggat ttgtctatag tcagtgtggc cttgcccttg aagttctcat tgtagtttgt   600
attaccatct ccaggagaaa tccctccaat ccactcaagt ccctgttcag gcctctgtct   660
caaccagttt atgtcaaagt atgtgaaggt gtagccagaa gccttgcagg acagtttcac   720
tgaagcccca ggctctacca gttcagcccc agactgctgc agctgcacct gggccat      777
```

```
<210> SEQ ID NO 25
<211> LENGTH: 5
<212> TYPE: PRT
<213> ORGANISM: Artificial
<220> FEATURE:
<223> OTHER INFORMATION: CDR sequence

<400> SEQUENCE: 25

Tyr Phe Asp Ile Asn
1               5

<210> SEQ ID NO 26
<211> LENGTH: 17
<212> TYPE: PRT
<213> ORGANISM: Artificial
<220> FEATURE:
<223> OTHER INFORMATION: CDR sequence

<400> SEQUENCE: 26

Val Ile Ser Pro Gly Asp Gly Asn Thr Asn Tyr Asn Glu Asn Phe Lys
1               5                   10                  15

Gly

<210> SEQ ID NO 27
<211> LENGTH: 11
<212> TYPE: PRT
<213> ORGANISM: Artificial
<220> FEATURE:
<223> OTHER INFORMATION: CDR sequence

<400> SEQUENCE: 27

Asp Gly Asn Phe Pro Tyr Tyr Ala Met Asp Ser
1               5                   10

<210> SEQ ID NO 28
<211> LENGTH: 16
<212> TYPE: PRT
<213> ORGANISM: Artificial
<220> FEATURE:
<223> OTHER INFORMATION: CDR sequence

<400> SEQUENCE: 28

Arg Ser Ser Gln Ser Leu Val Tyr Ser Asn Gly Asn Thr Tyr Leu His
1               5                   10                  15

<210> SEQ ID NO 29
<211> LENGTH: 7
<212> TYPE: PRT
<213> ORGANISM: Artificial
<220> FEATURE:
<223> OTHER INFORMATION: CDR sequence

<400> SEQUENCE: 29

Asn Val Ser Asn Leu Phe Ser
1               5

<210> SEQ ID NO 30
<211> LENGTH: 8
<212> TYPE: PRT
<213> ORGANISM: Artificial
<220> FEATURE:
<223> OTHER INFORMATION: CDR sequence

<400> SEQUENCE: 30

Ser Gln Ser Thr His Val Pro Thr
1               5
```

```
<210> SEQ ID NO 31
<211> LENGTH: 17
<212> TYPE: PRT
<213> ORGANISM: Artificial
<220> FEATURE:
<223> OTHER INFORMATION: CDR sequence

<400> SEQUENCE: 31

Gly Ile Ser Pro Gly Asp Gly Asn Thr Asn Tyr Asn Glu Asn Phe Lys
1               5                   10                  15

Gly

<210> SEQ ID NO 32
<211> LENGTH: 16
<212> TYPE: PRT
<213> ORGANISM: Artificial
<220> FEATURE:
<223> OTHER INFORMATION: CDR sequence

<400> SEQUENCE: 32

Arg Ser Ser Glu Ser Leu Val His Ser Asn Gly Asn Thr Tyr Leu His
1               5                   10                  15

<210> SEQ ID NO 33
<211> LENGTH: 7
<212> TYPE: PRT
<213> ORGANISM: Artificial
<220> FEATURE:
<223> OTHER INFORMATION: CDR sequence

<400> SEQUENCE: 33

Thr Val Ser Asn Arg Phe Ser
1               5
```

MONOCLONAL ANTIBODIES AND SINGLE CHAIN ANTIBODY FRAGMENTS AGAINST CELL-SURFACE PROSTATE SPECIFIC MEMBRANE ANTIGEN AS DIAGNOSTIC AND THERAPEUTIC TOOLS FOR PROSTATE CANCER

This application is a Divisional of, and claims priority under 35 U.S.C. §120 to, U.S. patent application Ser. No. 11/915,454, with a 371(c) filing date of Jan. 7, 2008 now U.S. Pat. No. 8,198,416, which was a U.S. national phase patent application under 35 U.S.C. §371 of PCT Patent Application No. PCT/EP2006/001917, filed on Mar. 2, 2006, and claims priority therethrough under 35 U.S.C. §119 to European Patent Application No. 05011536.9, filed May 27, 2005, the entireties of which are incorporated by reference herein. Also, the Sequence Listing filed electronically herewith is hereby incorporated by reference (File name: 2012-05-08T_033-014D_Seq_List; File size: 62 KB; Date recorded: May 8, 2012).

Cancer of the prostate is the most commonly diagnosed cancer in men and the second most common cause of death in the Western civilization. No curative treatment currently exists for this tumor after progression beyond respectable boundaries. Because of the significant mortality and morbidity associated with disease progression, there is an urgent need for new targeted treatments. In contrast to cancer in other organ systems, prostate cancer represents an excellent target for antibody therapy for a number of reasons, that include i) the prostate expresses tissue specific antigens, ii) the prostate is a non-essential organ and its destruction will not harm the host, iii) the sites of metastasis are lymph nodes and bone that receive high levels of circulating antibodies, and iv) the PSA serum levels provide a means to monitor therapeutic response.

Among several candidate markers that have been identified for prostate cancer, prostate specific membrane antigen (PSMA) seems to be most prominent. This type II transmembrane glycoprotein of about 100 KD consists of a short intracellular segment (amino acids 1-18), a transmembrane domain (amino acids 19-43), and an extensive extracellular domain (amino acids 44-750). PSMA may serve as a useful target for immunotherapy because it meets the following criteria: i) expression is primarily restricted to the prostate, ii) PSMA is abundantly expressed as protein at all stages of disease, iii) it is presented at the cell surface but not shed into the circulation, iv) expression is associated with enzymatic or signaling activity. PSMA is also expressed in the neovasculature of most other solid tumors, and therefore may be a target for specific anti-angiogenetic drug delivery.

Because of their target-oriented specificities, a lot of emphasis has been put on the development of monoclonal antibodies (mAbs) for diagnostic and therapeutic applications in cancer medicine. However, the in vivo use of mAbs is associated with serious problems, because of their size and immunogenicity. Therefore, research has focused on the development of smaller therapeutic antibodies with fewer side effects, better tumor accessibility and faster clearance rates. Genetic engineering has made it possible to construct single chain antibody fragments (scFv) which are potentially powerful tools for cancer therapy. These small antibodies are composed of the variable domains of the light chain ($V_L$) and the heavy chain ($V_H$) connected by a linker peptide. They show little immunogenicity, almost no toxic effects, an increased clearance rate, an improved uptake by the tumor and a better penetration into the tumor cells. Recombinant murine scFv can be established according to standard methods using either expression libraries from hybridomas or spleen cells of specifically immunized mice [Chowdhury et al., Mol. Immunol. 4 (1997), pp. 9-20].

The first published mAb (7E11-C5) against PSMA targets at the intracellular domain of the protein and was shown to be highly prostate specific [Horoszewicz et al., Anticancer Res. 7 (1987), p. 927-935]. Also, monoclonal antibodies against the extracellular domain of PSMA have been raised after immunization with the antigen. However, there is still a discrepancy between binding to the antigen on fixed cells and histological sections on the one hand and binding to viable tumor cells on the other hand.

Prostate specific membrane antigen (PSMA) is a prostate marker that is highly expressed in normal prostate as well as in prostate cancer. Its expression is increased in prostate cancer and is found primarily in the prostate.

Prostate specific membrane antigen (PSMA) is a unique membrane bound cell protein which is over expressed manifold on prostate cancer as well as in the neovasculature of many other solid tumors, but not in the vasculature of the normal tissues. This unique expression of PSMA makes it an important marker as well as a large extracellular target of imaging agents. PSMA can serve as target for delivery of therapeutic agents such as cytotoxins or radionuclides. PSMA has two unique enzymatic functions, folate hydrolase and NAALADase and it is found to be recycled like other membrane bound receptors through clathrin coated pits.

A radio-immuno-conjugate form of the anti-PSMA monoclonal antibody (mAb) 7E11, is commercially available as "ProstaScint®" which is currently being used to diagnose prostate cancer metastasis and recurrence. The PSMA epitope recognized by monoclonal antibody 7E11-C5.3 is located in the cytoplasmic domain of the prostate specific membrane antigen.

There are, however, also reports describing PSMA expression in non-prostatic tissues including kidney, liver and brain. A possible explanation therefore is provided by O'Keefe et al. (Prostate, Feb. 1, 2004; 58 (2) 200-10), namely that there is a PSMA-like gene which possesses 98% identity to the PSMA gene at the nucleotide level, which is expressed in kidney and liver under the control of a different promoter to the PSMA gene.

WO 01/009192 describes the development of human monoclonal antibodies to prostate-specific membrane antigen. Human anti-PSMA monoclonal antibodies were generated by immunizing mice with purified PSMA or enriched preparations of PSMA antigen. Such purified antigen is a denatured PSMA since it has been purified by immunoadsorption after cell lysis with ionic detergents.

WO 97/35616 describes monoclonal antibodies specific for the extracellular domain of prostate-specific membrane antigen. The immunizations were performed with a C-terminal peptide or a PSMA-expressing tumor membrane preparation. The mAbs do not bind specifically to PSMA-expressing cells and can therefore not be used for diagnostic or therapeutic purposes.

Bander et al., Seminars in Oncology, 2003, pp 667-677 and US 2004/0213791 respectively disclose monoclonal antibodies directed against prostate-specific membrane antigen. Since the immunization was performed with purified antigen, the monoclonal antibodies do not have a high cell binding and no scFv could be obtained from neither of these mAb.

WO 98/03873 describes the same antibodies as in US 2004/0213791 or binding portions thereof which recognize an extracellular domain of prostate-specific membrane antigen. It could not be shown that the binding portions of the antibodies do in fact bind to the antigen.

Fracasso et al., The Prostate, 2002, pp 9-23 describe anti-PSMA monoclonal antibodies which are chemically coupled to the ricine-A-chain. The constructs described in this article do not bind sufficiently specific to the target and have the generally described disadvantages of generation on immunotoxins.

It is one object of the present invention to provide superior means and constructs which help to differentiate with higher reliability between tumor cells and healthy cells which do express PSMA or a similar protein and PSMA-negative cells. Such constructs can be used to target more specifically prostate cancer.

It is another object to provide constructs which destroy specific prostate cancer cells which express PSMA.

Prostate-specific membrane antigen (PSMA) is an attractive target for immunotherapy of prostate cancer. However, on prostate cells PSMA is expressed with a specific tertiary and quaternary structure and antibodies elicited with isolated denatured PSMA do not efficiently recognize PSMA expressing tumor cells. Antibodies and scFv binding to denatured PSMA can be obtained after immunization with the isolated purified antigen. The present invention, however, allows the generation of high affinity antibodies and scFv against native cellular PSMA by a different immunization method which gives only a poor yield of positive clones. Only the later antibodies elicited with native PSMA may react with cell-surface PSMA and can be used as diagnostic and therapeutic tools.

Monoclonal antibodies (mAbs), single chain antibody fragments (scFv) and diabodies of the present invention were prepared according to conventional methods from mice spleen cells. However, the mice had been immunized with LNCaP cells and LNCaP cell lysate containing full-length native PSMA. In a preferred embodiment of the present invention the antigen, namely the full length native PSMA has been obtained after treatment of the cells, preferably LNCaP cells with a special lysis buffer called M-PER, mammalian protein extraction reagent which is commercially available from Pierce, Roquefort, Ill. The M-PER buffer uses a proprietary detergent in 25 mM bicine buffer (pH 7.6). Hybridomas and scFv were screened and selected by flow cytometry on PSMA-positive LNCaP cells after absorption with PSMA-negative DU 145 prostate cells. Additionally, they were tested for reactivity with purified PSMA. Resulting monoclonal antibodies and scFv were characterized by flow cytometry on LNCaP and PSMA-transfected DU 145 and by western blot with purified glycosylated and deglycosylated PSMA. In addition, immunocytology with LNCaP cells and immunhistochemistry on paraffin sections of prostate cancer samples was prepared.

In the course of the present invention three mAbs (3/F11, 3/A12 and 3/E7) could be obtained, that were reactive with viable LNCaP cells and PSMA-transfected DU 145 cells but not with other cell lines not expressing PSMA. Binding to LNCaP cells was very strong. At saturation concentrations (100 nM) the mean PE fluorescence intensity (MFI) was between 1000 and 1600. Reactivity with purified PSMA was stronger with the native form (ELISA) than with the denatured and deglycosylated protein (western blot). Immunohistochemistry on paraffin sections was specifically positive for epithelial cells with mAb E7.

From the mAb 3/A12 two scFv, called E8 and A5, were obtained by selection of recombinant phages on LNCaP cells and purified PSMA. The sequence of scFv E8 was identical to a scFv A4, which was obtained from the B-cell library of the same mouse. ScFv E8 was strongly reactive with LNCaP cells showing a MR of about 100 at saturation concentrations, whereas the MFI of scFv A5 was only about 40 under the same conditions. No or minimal binding was seen with other cell lines lacking PSMA expression. Binding of both scFv to purified denatured glycosylated and deglycosylated PSMA was weak. Furthermore, from mAb 3/F11 the scFv called D7 and for mAb 3/E7 the scFv called H12 was obtained.

In the present application we describe three mAb, which are different from those published by other authors with respect to high binding affinity and and high staining of PSMA expressing prostate cancer cells. The antibodies 3/F11, 3/A12 and 3/E7 do not only show a strong binding activity but also internalization into LNCaP cells as shown by immunofluorescence cytology and detection with confocal laser scanning microscopy. These mAbs were obtained after immunisation with full length native PSMA, which is in contrast to different published immunisation methods.

After immunization with purified denatured PSMA mAbs were obtained which were highly specific for the antigen, but had only a limited binding to PSMA expressing LNCaP cells and also were not internalized into the cells. These control data are not shown in the present application. There are a few anti-PSMA mAbs described in literature. However, the mean fluorescence intensity values were much lower than with the antibodies of the present invention.

Similarly to the mAbs, anti-PSMA scFv were generated after immunisation with denatured and native PSMA. With the denatured PSMA we obtained scFv highly specific to the antigen, but not binding to LNCaP cells (data not shown in the present application). In contrast, with native PSMA we obtained scFv with a high cell binding activity, but a poor binding to the isolated denatured antigen.

However, the problems identified in this and other trials with chemically linked immunotoxins are the development of antibodies against the immunotoxins, liver toxicity and vascular leak syndrome and also difficulties in producing large quantities of defined material. These problems are, at least in part, overcome by using recombinant DNA technology which makes the construction of less immunogenic and smaller immunotoxins feasible, and more easily permits the production of immunotoxins in large quantities. It is also believed that penetration into tumors should be better for small proteins than large conjugates. Therefore, recombinant immunotoxins were engineered by fusing the coding sequence of the scFv E8, H12, D7 and A5 and the toxin PE40. The central finding was that all recombinant immunotoxins effectively killed cultured prostate cancer cells in a dose dependent manner. Strong killing was found not only with the highly binding E8- with IC50 of about 0.05 nM, but also with the lower binding A5-fusion protein with IC50 of about 0.09 nM. Killing of not PSMA expressing prostate cancer cells was more than 2000-fold less. This may be traced back to residual bacterial proteins or other toxic agents in the immunotoxin preparations, because the same background could be observed in equally high concentrations with the scFv alone. The term IC50 is defined as the concentration in nM of the toxin which reduces cells proliferation to 50% of the cell proliferation without adding a toxin.

The antibodies and scFv described in this application specifically bind to native cell-surface PSMA and therefore will have value in diagnostic and therapeutic applications focusing on PSMA as a target antigen for prostate cancer.

Since PSMA is expressed on prostate cancer cells with a specific tertiary and quaternary structure, only antibodies against this cellular conformation may recognize and strongly bind to viable prostate cancer cells and PSMA-expressing tissue. Therefore, the aim of the present study was to generate such mAbs and scFv that can be used for therapeutic and diagnostic targeting of prostate cancer.

The present invention provides therefore an isolated monoclonal antibody or an antigen binding portion thereof which binds to prostate specific membrane antigen in its native form occurring on the surface of tumor cells which is linked to a label or a cytotoxic agent.

The term "isolated monoclonal antibody" refers to a glycoprotein comprising at least two heavy (H) chains and two light (L) chains interconnected by disulfid bonds. Each heavy chain is comprised of a heavy chain variable region (abbreviated as $V_H$) and a heavy chain constant region. The heavy chain constant region is comprised of three domains, namely CH1, CH2 and CH3. Each light chain contains a light chain variable region ($V_L$) and a light chain constant region ($C_L$). The $V_H$ and $V_L$ regions can be further subdivided into regions of hypervariability, which are also called complementarity determining regions (CDR) interspersed with regions that are more conserved. Those regions are also called framework regions (FR). Each $V_H$ and $V_L$ region is composed of three CDRs and four FRs arranged from amino terminus to carboxy terminus in the following order: FR1, CDR1, FR2, CDR2, FR3, CDR3, FR4. The variable regions of the heavy and light chains contain a binding domain that interacts with an antigen.

In FIGS. 13, 14 and 20, 21 the CDRs are marked by grey boxes. Those areas are important for the binding of the monoclonal antibody or the antigen binding portion thereof. The other areas are framework regions which can be replaced by other sequences, provided the three-dimensional structure which is required for binding is not disturbed. In case the structure of the construct is changed, there will be no sufficient binding to the antigen. Monoclonal antibodies derived from mouse may cause unwanted immunological side-effects due to the fact that they contain a protein from another species which may elicit antibodies. In order to overcome this problem the monoclonal antibodies or the antigen binding portions thereof may be humanized. The process of humanizing monoclonal antibodies is known to the person skilled in the art. The framework regions of a mouse mAb are replaced by the corresponding human framework regions. In order to maintain the preferred binding properties the sequences of the CDRs should be maintained as far as possible. It may be required, however, to perform some amino acid changes in order to optimise the binding properties. This can be performed by the person skilled in the art by standard proceedings. Furthermore by introducing a human framework it may be necessary to perform amino acid changes and/or deletions in order to improve the properties of the construct.

The term "antigen binding portion" of the monoclonal antibody refers to one or more fragments of such an antibody which retained the ability to specifically binding to the prostate specific membrane antigen in its native form. Examples of antigen binding portions of the antibody include a Fab fragment, a monovalent fragment consisting of the $V_L$, $V_H$, $C_L$ and $C_{H1}$ domains, an F(ab')$_2$ fragment, a bivalent fragment comprising two Fab fragments linked by a disulfid bridge at the hinge region, an Fd fragment consisting of the $V_H$ and $C_{H1}$ domain, an $F_v$ fragment consisting of the $V_L$ and $V_H$ domains of a single arm of an antibody, a dAb fragment which consists of a $V_H$ domain and an isolated complementarity determining region (CDR).

The isolated monoclonal antibody or antigen binding portion thereof according to the present invention can preferably be internalized by a tumor cell if it is used for therapeutic purposes. For diagnostic purposes an internalisation may not be required.

The isolated monoclonal antibody or an antigen binding portion thereof according to the present invention binds strongly to LNCAP cells but not to cells which lack expression of prostate specific membrane antigen.

The binding of the isolated monoclonal antibody or antigen binding portion thereof is measured by PE fluorescence intensity (MFI) which is preferably equal or higher than 40 for an scFv and preferably higher than 1000 for an mAb at saturating concentrations.

The binding properties of the isolated monoclonal antibodies or an antigen binding portion thereof to the native PSMA were compared by treating LNCAP cells with increasing concentrations of the first step anti-PSMA Ab followed by incubation with the second step PE-labeled antibody. From the resulting saturation curves the antibody concentration reaching 50% saturation of PSMA sites can be read. The three mAb 3/F11, 3/A12 and 3/E7 showed a high binding activity reaching 50% saturation of PSMA sites at approximately 16 nM (3/F11), 2 nM (3/A12) and 30 nM (3/E7). With the scFv a 50% saturation of PSMA sites was found at 10 nM (E8) and 60 nM (A5).

In order to determine the binding strength the PE (phycoerythin) fluorescence intensity (MFI) was measured. The MFI values were plotted against the antibody (or binding fragments thereof) concentration whereby the plateau value of MFI corresponds to 100% saturation with antigen. After having determined the top value (plateau corresponding to 100% saturation of antigen) the value corresponding to 50% of saturation can be easily determined By using the graph the corresponding concentration of the antibodies or binding fragments thereof in nM can be seen.

The isolated monoclonal antibody or an antigen binding portion thereof comprises a label which may be a particle which emits radioactive radiation. This particle may be a radioactive element in a form which can be linked to the construct, preferably in the form of a complex. For example an mAb labeled with $^{111}$Indium may be used as a radioimmunoscintigraphy agent in the detection of distant metastatic tumors in prostate cancer patients. Of course other suitable radioactive elements like $^{35}$S or $^{131}$I can be used.

Alternatively the isolated monoclonal antibody or antigen binding portion thereof may comprise a cytotoxic agent which is a cell toxic substance selected from the group consisting of toxins, for example taxol, cytocalasin B, gramicidin D, ethidium bromid, emetine, mitomycin, etopside, tenopside, vincristine, vinblastine, colchicin, doxorubicin, daunorubicin, dihydroxy antracin dione, mitoxantrone, mithramycin, actinomycin D, 1-dehydrotestosteron, glycocorticoids, procain, tetracaine, lidokaine, propranolol and/or puromycin.

In a preferred embodiment of the present invention an isolated monoclonal antibody or an antigen binding portion thereof comprises a partial amino acid sequence of at least 10 consecutive amino acids of SEQ ID NO:1 (scFv E8), SEQ ID NO:10 (scFv A5), SEQ ID NO:20 (scFv H12) and/or SEQ ID NO:22 (scFv D7). In a preferred embodiment the monoclonal antibody or antigen binding protein thereof comprises at least 25 or, more preferred, at least 35 and most preferred at least 50 consecutive amino acids of SEQ ID NO:1, SEQ ID NO:10, SEQ ID NO:20 and/or SEQ ID NO:22, respectively.

In a preferred embodiment the isolated monoclonal antibody or antigen binding portion thereof comprises at least one of the CDRs having SEQ ID NO:2-SEQ ID NO:7 and/or SEQ ID NO:11 to 16. More preferably such construct comprises at least 3 and more preferably at least 5 of those CDR sequences. In a similar manner the CDRs can be deduced from FIGS. 20 and 21 wherein the CDR sequences are designated.

It is a further aspect of the invention to provide DNA sequences which can be used for the preparation of monoclonal antibodies or binding fragments thereof. SEQ ID NO:8 and 9 relate to scFv E8 and SEQ ID NO:17 and 18 relate to scFv A5. SEQ ID NO:19 and 23 relate to scFv H12 and SEQ ID NO:21 and 24 relate to scFv D7. The sequences report the coding strand and the complementary strand thereto. SEQ ID NOS:9 and 18 are shown in the 5'→3' orientation. The polynucleotides of the present invention comprise a contiguous sequence of at least 20, preferably 50 and more preferably 75 and most preferred at least 100 nucleotides of the group consisting of SEQ ID NOS: 8, 9, 17, 18, 19, 21, 23 and 24. The sequence coding for the CDR are in particular preferred.

It is one aspect of the present invention to provide a pharmaceutical composition comprising an isolated monoclonal antibody or an antigen binding portion thereof as described in the present application. The pharmaceutical composition of the present invention comprises the monoclonal antibody or an antigen binding portion thereof together with pharmaceutically acceptable additives. Preferably such a composition is prepared for intramuscular or intraveneous injection. Alternatively the antibody may be provided in a depot formulation which allows the sustained release of the biologically active agent over a certain period of time which may range preferably from one to six months. Such a sustained release formulation may comprise a biodegradable polymer like a polylactide or polylactide/polyglycolide copolymer which is degraded over a prolonged period of time in the human body whereby the antibody or the antigen binding portion thereof preferably having a toxine is released in a controlled manner over a certain period of time.

The isolated monoclonal antibody or an antigen binding portion thereof may be used for the preparation of a medicament for the treatment of cancer, in particular prostate cancer.

Alternatively the invention provides a diagnostic kit for the detection of tumor cells comprising an isolated monoclonal antibody or an antigen binding portion thereof. In such embodiments the label allows the detection of the construct with suitable detection devices.

The invention provides also a method for the in vitro identification of tumor cells by which the tumor cells to be identified are contacted with an isolated monoclonal antibody or an antigen binding portion thereof which carries a label which can be detected by suitable analytical devices. The label allows the diagnostic identification of tumor cells, for example in section of human tissues obtained after surgery or biopsy.

BRIEF DESCRIPTION OF THE DRAWINGS

FIG. 2: Immunfluorescence cytology: Binding of a) mAb 3/F11 b) mAb 3A/12 c) 3E7 to LNCaP cells. The left pictures show a control staining with 4',6-Diamidino-2-phenylindole (DAPI).

FIG. 3: Immunfluorescence cytology: Internalization of a) mAb 3/F11 b) mAb 3/A12 c) 3E7 in LNCaP cells. The left pictures show control staining with 4',6-Diamidino-2-phenylindole (DAPI).

FIG. 9: immunocytology of scFv E8 on LNCaP cells

FIG. 13: Sequence of scFv E8. DNA sequence is given as well as amino acid sequence whereby the region of the CDWs is identified by a marked area.

FIG. 14: Sequence of scFv A5. DNA sequence is given as well as amino acid sequence whereby the region of the CDWs is identified by a marked area.

FIG. 20: shows the sequence of scFv H12. The amino acid sequence is given in the one-letter-code in the first line (corresponding to SEQ ID NO:20). The coding strand is shown on the second line (SEQ ID NO:19) and the complementary strand is shown in the third line. This sequence corresponds to SEQ ID NO:23. The CDRs are specifically designated as CDR H1, H2, H3, L1, L2 and L3. The nucleic acid sequences coding for the CDR regions are shown on a grey background.

FIG. 21: shows the sequence of scFv D7. The amino acid sequence is shown on the first line in the one letter code. This sequence corresponds to SEQ ID NO:22. The coding nucleic acid strand is shown on the first line. This sequence corresponds to SEQ ID NO:21 and the complementary strand is shown on the third line. This sequence corresponds to SEQ ID NO:24. The CDR regions H1, H2, H3, L1 and L2 are shown in the sequence. The nucleic acid sequences coding for those regions are shown on a grey background.

EXAMPLES

Figure 1:
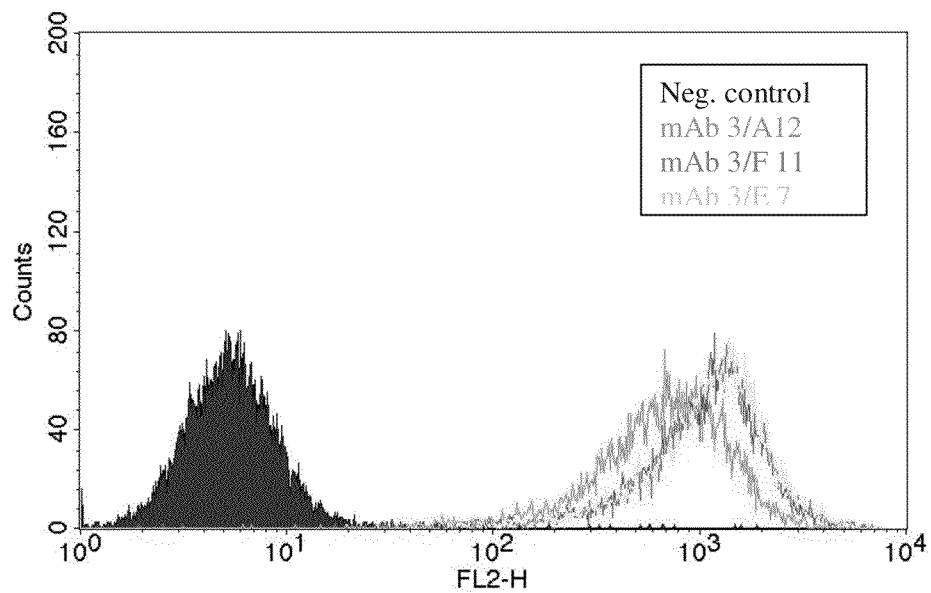
FIG. 1: FACS-analysis of the mAb 3/F11, 3/A12 and 3/E7 binding to the surface of PSMA-expressing LNCaP cells at saturation concentrations
Figure 1A:
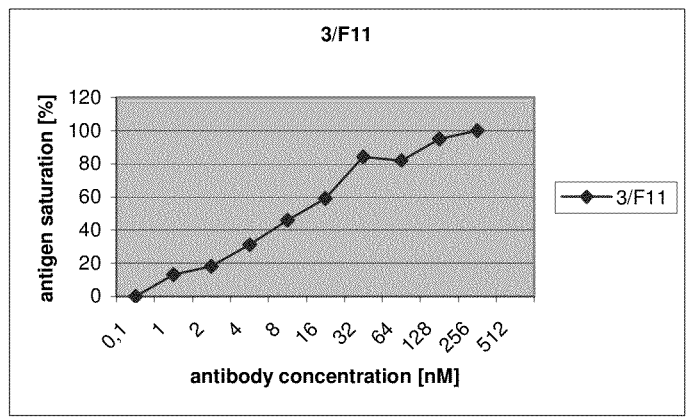
FIG. 1*a-c*: Antigen saturation curves of mAb 3/F11 (a), 3/A12 (b), 3/E7 (c)
Figure 1B:
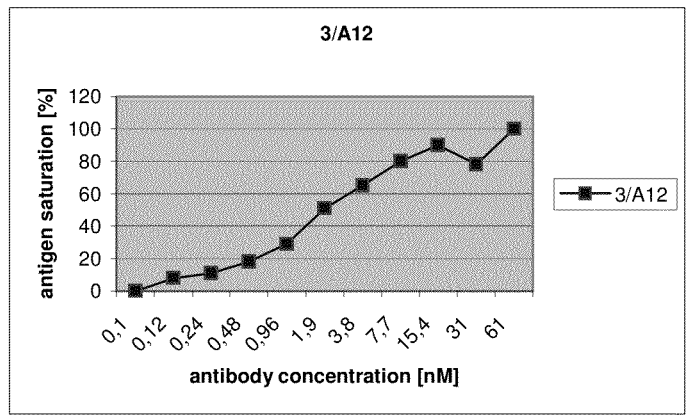
Figure 1C:
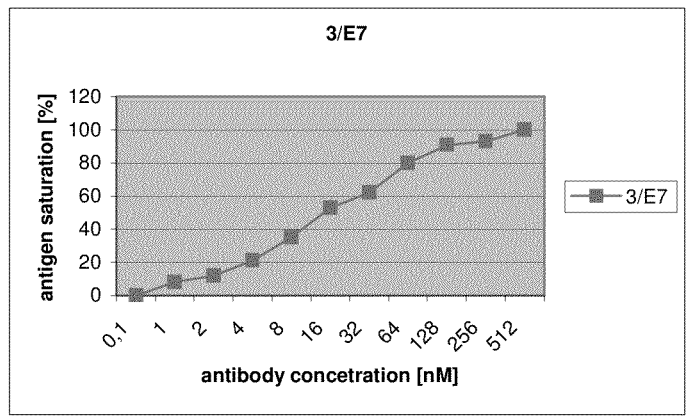

The present invention is further illustrated by the following examples.

Example 1 a) Preparation of PSMA

The human prostate carcinoma cell lines LNCaP, DU 145, PC-3 and HeLa as well as the hybridoma 7E11-C5.3 (IgG1-k, PSMA) were purchased from the American Type Culture Collection (ATCC), Rockville, Md., USA. LNCaP, DU 145 and HeLa were cultured in RPMI 1640 medium, PC-3 in F12 Nutrimix medium, both supplemented with penicillin (100 000 U/l), streptomycin (100 mg/l) and 10% FCS at 37° C. in a humidified atmosphere of 5% $CO_2$. For the generation of LNCaP cells expressing unglycosylated PSMA on their surface 2 µg/ml tunicamycin (ICN Biomedicals) were added to the medium for 48 h.

Fixed LNCaP cells were obtained by treatment with 4% paraformaldehyd for 10 min at RT, and then thoroughly washing with PBS.

For preparing purified PSMA, $10^8$ LNCaP cells were washed with PBS and then lysed in PBS containing 1% IGEPAL for 20 min at room temperature. After centrifugation at 10,000 g the supernatant was given on a 7E11-C5 affinity chromatography column (Amersham Biosciences, Uppsala, Sweden) and PSMA was eluted with 100 mM glycine buffer pH 2.5 containing 1% Triton X-100. After neutralisation the protein was extensively dialyzed with PBS.

For preparation of deglycosylated PSMA, 1/10 vol glycoprotein-denaturing buffer (BioLabs), was added to the solution with purified PSMA and heated for 10 min at 100° C. Then 1/10 vol 10% NP-40 (10%) and 50 U PNGase per µg PSMA was added and incubated at 37° C. for 1 h.

For preparation of a LNCaP cell lysate containing full length native PSMA, cells were lysed with M-PER reagent (Pierce) for 10 min and then centrifuged at 15,000 rpm for 30 min at 4° C. The supernatant containing native full length PSMA was collected (M-PER-lysate). The high molecular fraction (100 to 600 KD) of this lysate was separated by HPLC on a Biosil 250 size exclusion column b) Transfection of Full Length PSMA into DU 145 and PC3 Cells

Full length PSMA was cloned in two fragments (fragment 1 from by 262 to the unique EcoRI restriction site at by 1573 and fragment 2 from position 1574 to 2512) into the vector pCR3.1 (Invitrogen). Transient transfection was obtained by adding a mixture of 4 µg DNA and 10 µl Lipofectamine (Invitrogen) in 500 µl RPMI medium to $10^6$ cells according to the manufacturer's protocol. After 48 h incubation the transient transfected cells were used for testing.

Example 2

Immunization of Mice

Four-month old female Balb/c mice were immunized intraperitoneally with 300 µg M-PER lysate from LNCaP cells or with the high molecular HPLC fraction of the lysate, or with $10^6$ LNCaP cells, fixed with 2% paraformaldehyde. These preparations were mixed 1:1 with complete Freund's adjuvant. Each mouse received 4 or 5 immunizations at 2-week intervals. Four days after the last immunization spleen cells were collected and either used for the preparation of hybridomas or a B-cell library.

Example 3

Preparation of a B-Cell Library

The mouse spleen was washed in phosphate buffered saline (PBS), minced to small pieces, washed again in PBS and then gently homogenized in a "loose-fitting" hand homogenizer. The resulting single cell suspension was overlayered onto Ficoll (Pharmacia, Freiburg, Germany) and centrifuged at 400 g for 20 min at room temperature. Interphase B cells were isolated with CD19 microbeads according to the manufacturer's instructions (Miltenyi, Bergisch Gladbach, Germany). $10^6$ B-cells were lysed in 350 µl of a solution consisting of 4 M guanidine thiocyanate, 25 mM sodium citrate, 0.5% sodium N-laurosylsarcosinate and 100 mM 2-mercaptoethanol.

Example 4 a) Preparation of Hybridomas

The spleen was aseptically removed and a single cell suspension was prepared in RPMI-1640 medium without serum. The splenocytes were added to SP2/0 myeloma cells at a ratio of 10:1 and the fusion and selection was performed to established procedures [Galfre et al., Nature (1979), p. 131-133].

Hybridoma supernatants were tested by FACS on LNCaP and DU145 cells and by an ELISA with purified PSMA as solid phase. Monoclonal antibodies were purified using a protein G column (Pharmacia).

b) Isotype Determination of the mAbs

Ig-isotypes of the anti-PSMA mAbs were determined by ELISA using either unlabelled (solid phase) or peroxidase-labeled (tracer) anti-isotype specific antibodies (Southern Biotechnology Associates, Birmingham, Ala.).

c) Isolation and Characterization of Anti-PSMA Conformational Monoclonal Antibodies From Balb/c mice which were immunized 5 times with the M-PER-lysate from LNCaP cells, spleen cells were fused with SP2/0 cells according to established methods. Positive hybridomas were selected by flow cytometry with LNCaP cells and ELISA on purified PSMA. By this way three positive clones were obtained. The corresponding mAbs with their isotypes were 3/F11 (IgG2a), 3/A12 (IgG1) and 3/E7 (IgG2b).

d) Characterization of mAbs

By flow cytometry it could be observed that the three mAbs and stained LNCaP cells bind very well with a percentage of positive cells ranging from 95% to 98%. The shape of the curves of fluorescence versus number of events suggesteds that PSMA is homogeneously distributed within the LNCaP cell population (FIG. 1). To evaluate the binding specificity of the anti-PSMA mAbs, PSMA-negative DU145, PC3 cells, HeLa and Jurkat cells were also stained and analyzed by flow cytometry. All three mAbs did not stain the PSMA-negative cells (percentage of positive cells ranging from 0.04% to 2%).

The binding properties of the three antibodies were compared by treating LNCaP cells with increasing concentrations of the first step anti-PSMA mAb followed by incubation with a saturating amount of a second step PE-(phycoerythin)-labeled goat antibody followed by cytofluorometry analysis. At antigen saturation concentrations [100 nM] the corrected mean PE (phycoerythin) fluorescence intensity was about 1000 for mab 3A12, and about 1400 for mAb 3F11 and about 1600 for mAB 3E7. As shown for mAb 3A12 the MFI was 5-fold lower on LNCaP cells expressing unglycosylated PSMA (grown with tunicamycine).

Figure 4:
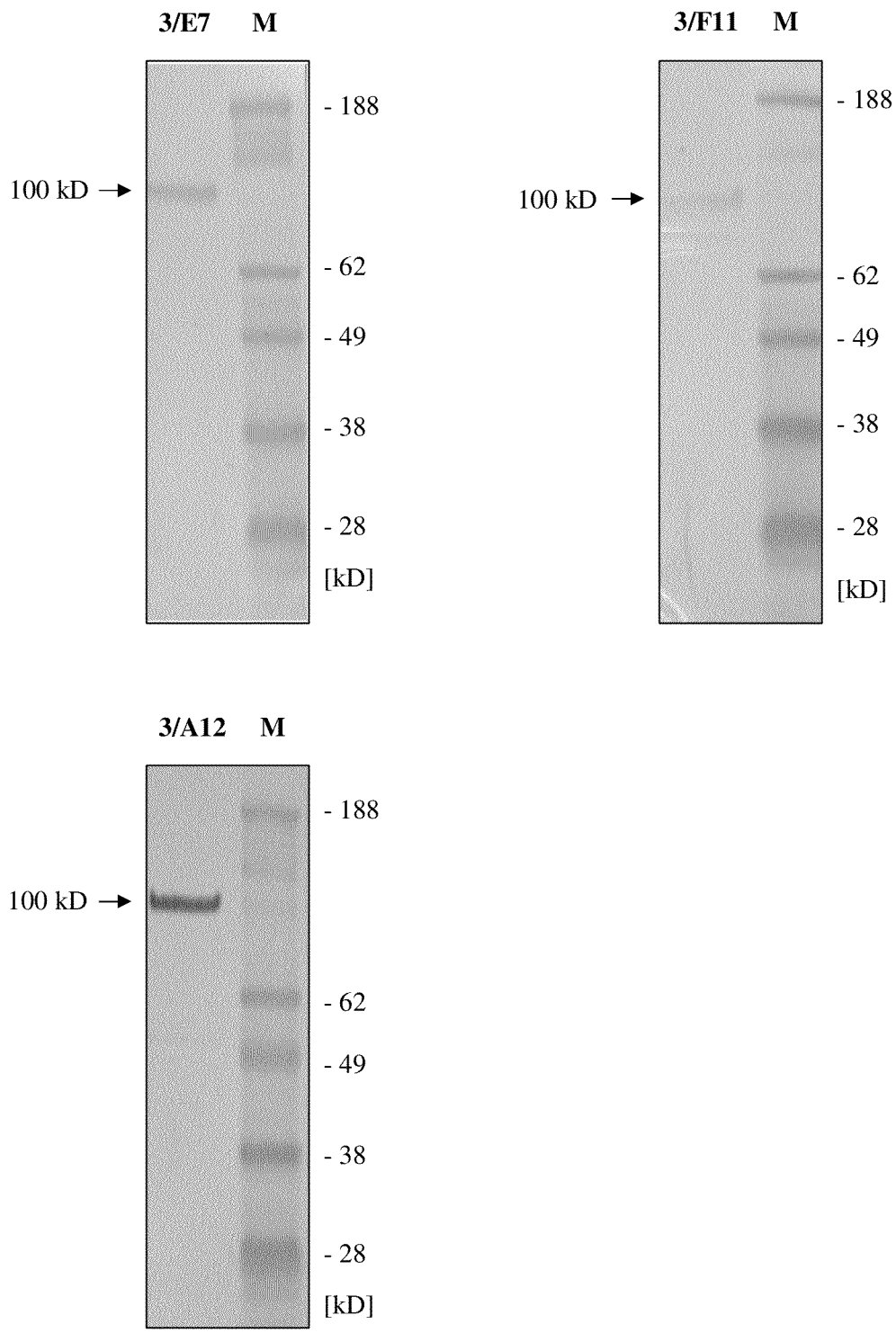
FIG. 4: Western blot with purified PSMA and the mAbs 3/E7, and 3/A12 and 3/F11
Figure 5:
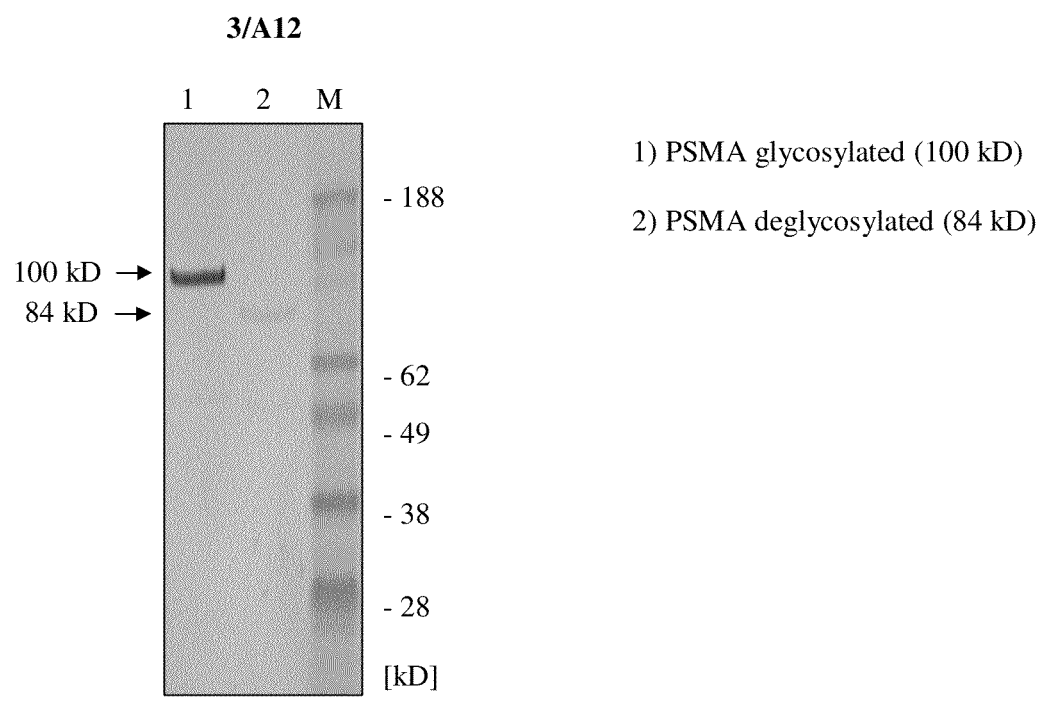
FIG. 5: Western blot with glycosylated and deglycosylated PSMA and mAb 3/A12

By immunofluorescence cytology and detection with a laser scanning confocal microscope a strong binding of the three mAbs to LNCaP cells (FIG. 2) and also an internalization into these cells could be shown (FIG. 3). All mAbs were positive in an ELISA with purified PSMA as solid phase. With denatured PSMA the mAbs showed a signal at about 100 KD in western blot (FIG. 4) whereas the blot with deglycosylated PSMA was weak giving a signal at about 84 KD, which corresponds to literature data (FIG. 5).

Figure 6:
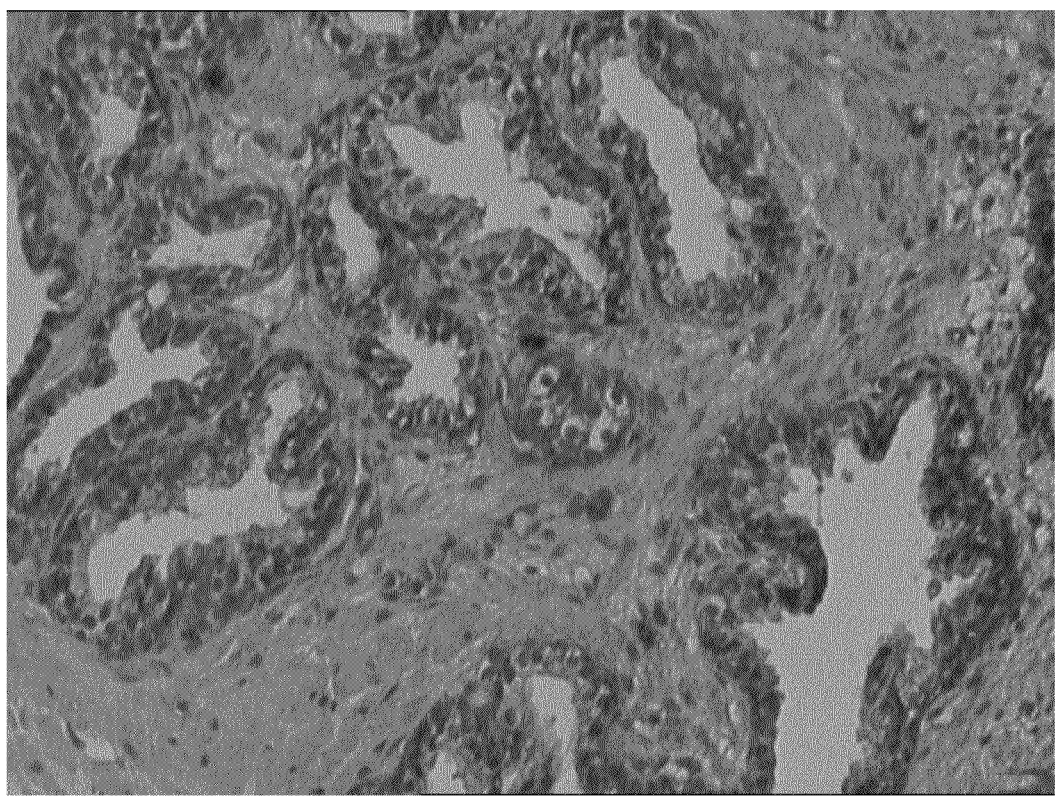
FIG. 6: Immunhistochemistry of mAb 3/E7 on a paraffin section of prostate cancer FIG. 7*a/b*: FACS-analysis of the scFv E8 (a), and A5 (b) on PSMA-expressing LNCaP cells at saturation concentrations FIG. 7*c/d*: Antigen saturation curves of scFv E8 (c) and A5 (d)

Immunohistochemistry on paraffin sections of prostate cancer was positive with mAb 3/E7 but not with mAbs 3/F11 and 3/A12 (FIG. 6). Data are summarized in Table 1.

TABLE 1

Characterization of 3 monoclonal antibodies against cell-surface PSMA

| Hybridoma | Isotype | FACS LNCaP [MFI]* | FACS PSMA-transf. DU *[MFI] | ELISA PSMA | Blot PSMA | Blot degl. PSMA | Immunohisto-chemistry |
|---|---|---|---|---|---|---|---|
| 3/F11 | IgG2a | 1400 | 105 | pos | pos | (pos) | neg |
| 3/A12 | IgG1 | 1000 | 110 | pos | pos | (pos) | neg |
| 3/E7 | IgG2b | 1600 | 90 | pos | pos | (pos) | pos |

MFI = mean fluorescence intensity at scFv concentration reaching antigen saturation (background staining with secondary antibody alone is subtracted)
(pos) = slightly positive From these data it is concluded that the 3 mAbs show a very strong and highly specific binding to native and denatured PSMA. Although the binding to deglycosylated PSMA is weaker, a sugar specifity can be excluded from the fact that no binding is seen to cells that do not express PSMA.

Example 5

Preparation of a scFv Expression Library in the Phagemid pSEX

From the B-cell library or from hybridoma cells total RNA and mRNA was isolated with silicagel-based membranes (Rneasy, Qiagen, Hilden, Germany) according to the manufacturer's protocol. cDNA synthesis was performed at 42° C. for 60 min in a final volume of 50 µl which contained 25 µl of denatured RNA, 10 µl 5× buffer (Promega, Heidelberg, Germany), 5 µl of 10 mM dNTP (dATP, dCTP, dGTP, dTTP, Promega), 1.5 µl RNAsin (40 U/µl, Promega) 2.5 µl of 150 µM random hexamer primers, and 2.5 µl of AMV reverse transcriptase (10 U/µl, Promega). Then the encoding regions of the heavy-chains and the gamma and kappa chains were amplified by PCR as previously described by Orum et al. [Nucleic Acies Res. (1993), 4491-4498]. For each chain 25 separate reactions were carried out by combining 25 different constant region forward primers with one corresponding reverse primer. The amplified products for the light chains and the heavy chains were purified by agarose gel electrophoresis.

The PCR products for the light chains were digested with MluI and NotI, and ligated into the phagemid pSEX81 [Dübel et al., Gene (1993), 97-101] using a molar ratio of 1:3 (2 µg vector, 400 ng insert). The products of one ligation were used for the electroporation of 50 µl electrocompetent E. coli XL1 blue cells (Stratagene) according to the supplier's protocol. The bacteria were plated on nine 80 mm diameter agarose plates containing 100 µg/ml ampicillin and 0.1 M glucose (SOB-AG) of and incubated overnight at 30° C. Bacteria were isolated by adding 3 ml 2× YT medium on each plate, scraping them off with a sterile glass spreader and pelleted at 3,000 g for 15 min From these bacteria plasmid DNA was isolated which revealed the Vl sublibrary. Then the PCR products for the heavy chain and the Vl sublibrary were digested with NcoI and HindIII. Ligation was prepared at a ratio of 3:1 (2 µg sublibrary and 400 ng insert). Transformation by electroporation, plating and collection of transformed bacteria was done as described for the Vl sublibrary. From nine 80 mm diameter SOB-AG plates a total of 18 ml $V_H V_L$ library was obtained.

Example 6

Production and Selection of Antibody-Displaying Phage a) Production

In the $V_H V_L$ library in phagemid pSEX the antibody genes are fused in frame with gene III, which encodes the minor surface protein gIIIp of the filamentous phage. Therefore, production of recombinant phagemid particles displaying the antibody on the surface requires infection of the phagemid-carrying bacterial cell with the replication defective phage M13KO7 [14]. M13KO7 was added to a 10 ml library culture at a multiplicity of 10. After incubation at 37° C. for 90 min the cells were pelleted and resuspended in 15 ml 2× YT-medium containing 100 µg/ml ampicillin, 10 µg/ml tetracycline and 50 µg/ml kanamycin. The culture was incubated overnight at 37° C. at 250 rpm, then chilled on ice and centrifuged to remove cells. The supernatant containing the phages was mixed with ⅕ volume of an aquous solution containing 20% PEG 8,000 and 14% NaCl and incubated 1 h at 4° C. Then a centrifugation step of 30 min at 4° C. and 6,200 g was added. The pellet containing the phages was resuspended in 2 ml 10 mM Tris/HCl pH 7.5, 20 mM NaCl, 2 mM EDTA pH 7.5 and used for panning.

b) Panning to Select for Antigen- and Cell-Binding Clones

Panning on purified PSMA was done in 96 well Maxi-Sorb microtiter plates (Nunc) which were coated with a solution of purified PSMA (100 µl/well, 12 µg/ml PSMA in PBS) and blocked with 4% non-fat milk/PBS. One ml of purified recombinant phages (circa $10^{11}$) were incubated in 1 ml 4% non-fat milk/PBS supplemented with 15 µl 10% Triton X100 for 15 min and then allowed to bind to 8 wells coated with PSMA for 2 h at 37° C. After 20 rounds of washing with PBS/Tween (0.1%) the bound phages were eluted with 0.1 M Glycin-Puffer pH 2.2. For panning on viable LNCaP cells phages were previously absorbed on DU 145 cells. For this procedure 1 ml (circa $10^{11}$) recombinant phages were incubated in 2% non-fat milk/PBS for 15 min and then with $10^7$ DU 145 cells for 1 h at room temperature on a shaker. Then the cells were centrifuged and the supernatant with non absorbed phages was incubated with $10^6$ LNCaP cells for 1 h at room temperature on a shaker. After 10 washing rounds with 2% non-fat milk/PBS and 5 rounds with PBS the bound phages were eluted with 50 mM HCl with subsequent neutralization with 1 M Tris-HCl (pH 7.5).

*E. coli* TG1 cells were infected with the eluted phages, plated on SOB-AG plates and incubated overnight at 30° C. An aliquot of the eluate was used for titration. The selection procedure was repeated three to six times.

c) Small Scale Phage Rescue

From the titration plate 96 individual colonies were isolated and each transferred into one well of a 96-deep-well microtiter plate filled with 500 µl 2× YT medium containing 100 µg/ml ampicillin and 0.1 M glucose (YT-AG) and incubated overnight at 37° C. (master plate). Then 40 µl of saturated culture from each well of the master plate were transferred to the corresponding well of a new plate containing 400 µl of 2× YT-AG medium.

To each well about $1\times10^{10}$ M13KO7 helper phages were added and incubated on a shaker for 2 hours at 37° C. Then the plate was centrifuged and the pellet suspended in 2× YT medium supplemented with 100 µg/ml ampicillin, 10 µg/ml tetracycline, and 50 µg/ml kanamycin and incubated at 29° C. and 240 rpm overnight. After centrifugation the supernatant containing the rescued phagemids was removed and used for phage ELISA and flow cytometry.

d) Phage-ELISA

Microtiter plates were coated with purified PSMA (1.5 µg PSMA/ml PBS) overnight and then blocked with 2% non-fat milk/PBS. To each well 200 µl of rescued phagemids, preincubated 1:1 with 2% non fat-milk/PBS, were added and incubated for 2 h at room temperature. After five washing steps with PBS-Tween, bound phages were detected with 200 µl/well anti-M13 antibody conjugated to horseradish peroxidase (Pharmacia) for 2 h at room temperature. Development was carried out with 3,3',5,5'-tetramethylbenzidine as substrate.

e) Isolation and Characterization of Anti-PSMA Conformational scFv

For generation of anti-PSMA conformational scFv a $V_H V_L$ library in the phagemid pSEX was constructed from the B cell library of a mouse immunized with M-PER-lysate of LNCaP cells. This library had a complexity of $10^7$. In a similar way a $V_H V_L$ library was prepared from the monoclonal antibody 3/A12, which was obtained from the same mouse immunized with LNCaP lysate. This $V_H V_L$ library had a complexity of $10^5$. To isolate phages displaying cellular PSMA binding scFv on their surface, six rounds of panning were performed alternatively on LNCaP cells after absorption with DU-145 cells in polystyrene tubes and in microtiter plates coated with 20 µg/ml purified PSMA. After three, four and six panning rounds isolated phagemid colonies were grown and phage particles were rescued by infection with M13KO7. Analysis of 800 phage clones from the B-cell library by flow cytometry with LNCaP cells and ELISA on purified PSMA showed one positive clone called E8. Out of the $V_H V_L$ library from mAb 3/A12 two positive clones were obtained after the fourth panning round called A4 and A5. By sequencing it was found that A4 was identical to E8.

The coding region of the scFv E8 and A5 were transferred from the phagemid pSEX into the expression vector pHOG, containing C-terminal c-myc and His-tags. The sequences with the corresponding CDRs are given in FIG. 13 and FIG. 14. The regions coding for the CDR's of the antigen binding portions are marked in FIGS. 13 and 14. Those sequences should not be changed whereas the other parts of the sequence which are not marked can be changed. The appropriate three-dimensional structure must, however, be maintained.

Figure 7:
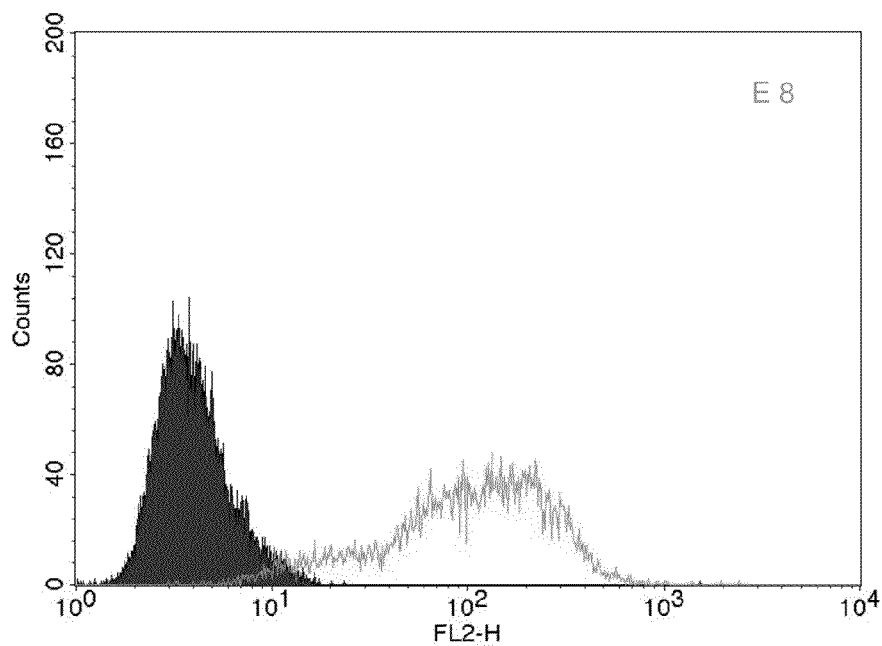
Figure 7:
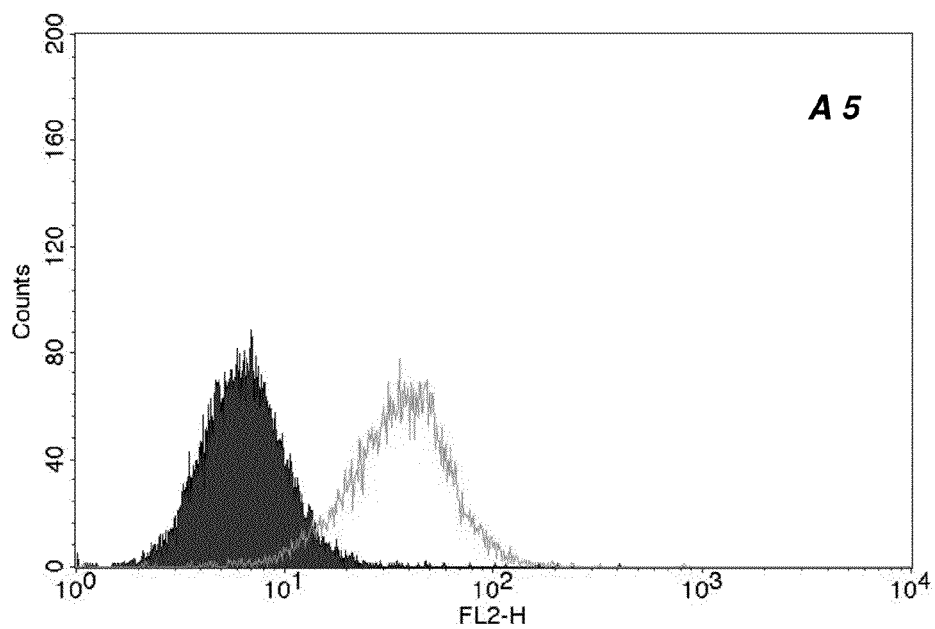
Figure 7C:
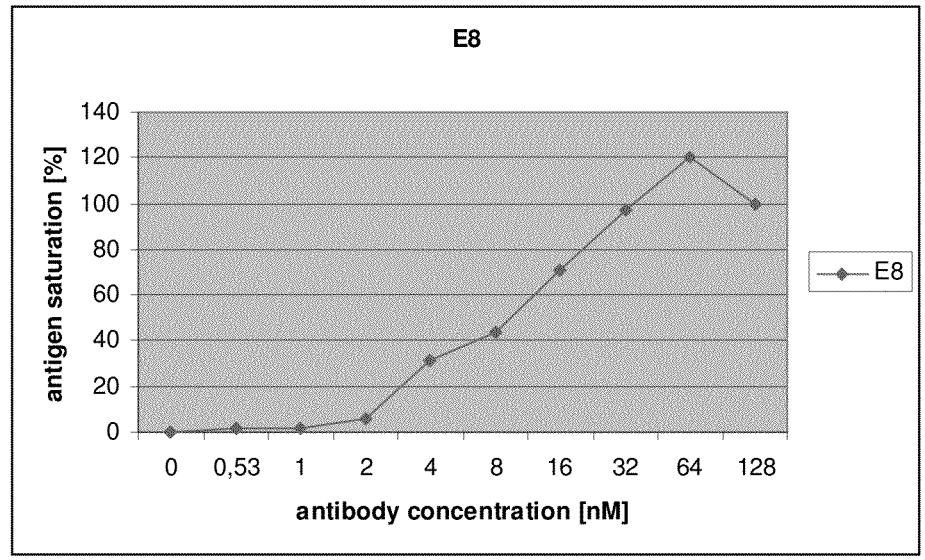
Figure 7D:
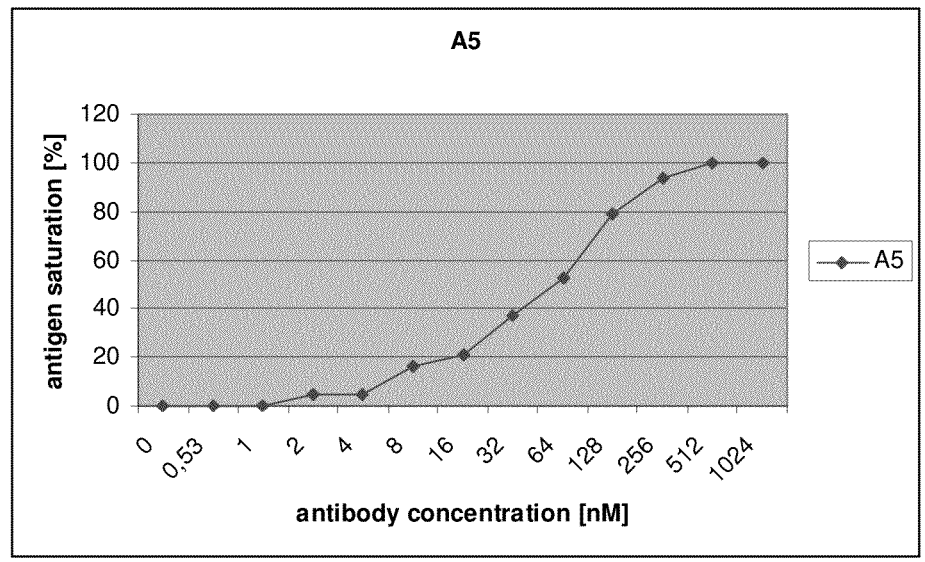
Figure 8:
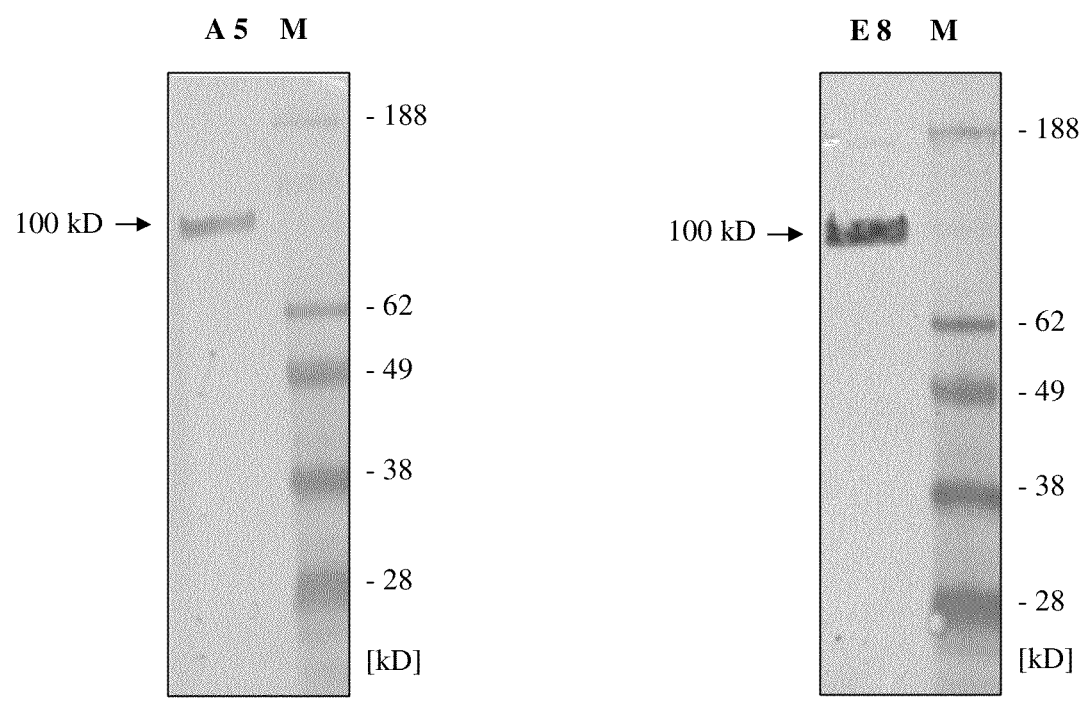
FIG. 8: Western blot with purified PSMA and the scFv A5 and E8
Figure 10:
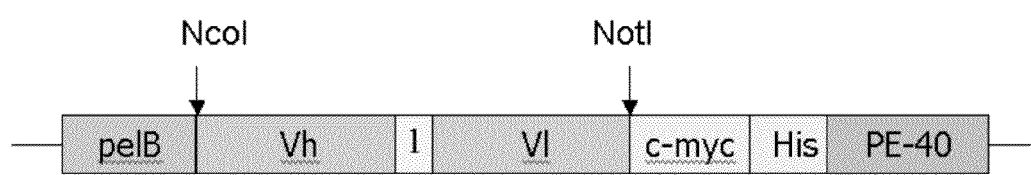
FIG. 10: construct of the immunotoxin E8-P40

The scFv E8 strongly reacted with viable LNCaP cells as measured by flow cytometry with MFI values of about 100 at saturating concentrations, whereas binding of A5 was much weaker with MFI-values of about 40 at saturating concentrations (FIG. 7). In contrast, binding to purified PSMA as solid phase in an ELISA was weak for E8 and somewhat stronger for A5. A similar pattern was seen in western blots with denatured glycosylated and deglycosylated PSMA (FIG. 8). By immunofluorescence cytology with LNCaP cells and detection by confocal laser microscopy a very good binding of the scFv E8 and internalization could be shown (FIG. 9). Data of the scFv are summarized in Table 2.

TABLE 2

Characterization of 2 scFv against cell-surface PSMA

| ScFv | Origin | FACS LNCaP [MFI] | FACS PSMA-transf. DU [MFI] | ELISA PSMA | Blot PSMA | Blot degl. PSMA |
|---|---|---|---|---|---|---|
| E8 = A4 | B-cell library and mAb A12 | 100 | 70 | pos | (pos) | (pos) |
| A5 | MAb A12 | 40 | | pos | pos | (pos) |

MFI = mean fluorescence intensity at scFv concentration reaching antigen saturation (background staining with secondary antibody alone is subtracted)
(pos) = slightly positive Example 7

ScFv Expression and Purification

ScFv fragments were expressed in *E. coli* XL1-Blue (Stratagene) using the secretion vector pHOG 21 which contains the sequences for the His-6 and c-myc-tag in a C-terminal position of the scFv [Kipriganov et al., J Immunol. Methods (1997), p. 69-77]. *E. coli* bacteria transformed with pHOG plasmids were grown overnight in 2× YT-AG-medium, then diluted 1:20 and grown as 600 ml cultures at 37° C. When cultures reached OD 0.8, bacteria were pelleted by centrifugation at 1,500 g for 10 min and resuspended in the same volume of fresh YT medium containing 50:g/ml ampicillin, 0.4 M sucrose and 1 mM IPTG. Then growth was continued at room temperature for 18 to 20 h. Cells were harvested by centrifugation at 5,000 g for 10 min and 4° C. To isolate soluble periplasmic proteins, the pelleted bacteria were resuspended in 5% of the initial volume of ice-cold 50 mM Tris-HCl, 20% sucrose, 1 mM EDTA pH 8.0. After a 1 h incubation on ice, the spheroblasts were centrifuged at 20,000 g at 4° C. for 30 min yielding soluble periplasmic extract in the supernatant. The periplasmic extract was concentrated using Amicon YM 10 membranes with a 10 kDa cut-off (Amicon, Witten, Germany) followed by thorough dialysis against 50 mM Tris-HCl, M NaCl, pH 7.0.

Purification was achieved by immobilized metal affinity chromatography. This was performed using a 1 ml column of chelating Sepharose (Pharmacia) charged with $Cu^{2+}$ and equilibrated with a buffer containing 50 mM Tris-HCl and 1 M NaCl, pH 7.0. The periplasmatic extract was loaded, washed with twenty column volumes of equilibration buffer containing 30 mM imidazole and then eluted with the same buffer containing 250 mM imidazole. Eluted material was dialyzed against PBS.

Determination of the protein content was performed with the Micro BCA Protein Reagent Kit (Pierce) according to the manufacturer's instructions.

Protein induction was obtained with IPTG and the scFv yield from a 600 ml *E. coli* XL1 culture was about 20 μg.

Example 8

Flow Cytometry

LNCaP, DU 145, and PC3 cells were freshly harvested from tissue culture flasks and a single cell suspension was prepared in PBS with 3% FCS and 0.1% $NaN_3$. Approximately $10^5$ cellswere incubated with 50 μl of rescued phagemids, preincubated 1:1 with 2% non-fat milk/PBS, 1 h on ice. After 3 rounds of washing with PBS 25 μl/well anti-c-myc monoclonal antibody 9E10 (10 μg/ml; Becton Dickinson) or when phages were tested 25 μl/well anti-M13 antibody (10 μg/ml; Pharmacia) were added and incubated 40 min on ice. After washing 3 times with PBS the cells were incubated with 100 μl of PE-labeled goat anti-mouse IgG (Becton Dickinson) for 40 min on ice. The cells were then washed again and resuspended in 100 μl of a solution containing 1 μg/ml propidium iodide (Sigma, Deisenhofen) in PBS with 3% FCS and 0.1% $NaN_3$ in order to exclude dead cells. The relative fluorescence of stained cells was measured using a FACScan flow cytometer and the CellQuest software (Becton Dickinson Mountain View, Calif.).

Example 9

Immunofluorescence Cytology

LNCaP cells were grown on glass coverslips for 24 hours. For fixation, cells were treated with 2% paraformaldehyde in PBS for 30 min at RT, which does not permeabilize the cell membrane, washed with 1% BSA-PBS, quenched for 10 min in 50 mM $NH_4Cl$ in PBS, and rinsed with 1% BSA-PBS. Primary monoclonal antibody at 4 μg/ml in 1% BSA-PBS was added and incubated for 60 min at 4° C. FITC-labeled goat anti-mouse secondary antibody (2 μg/ml; Southern Biotechnology Associates Inc. Birmingham, USA) was incubated for 30 min and washed extensively with 1% BSA-PBS. Slides were mounted in Vectashield (Vector Laboratories, Inc. Burlingame, Calif.).

For internalization experiments the primary antibody was incubated for 30 min at 37° C. before fixation of the cells with 2% paraformaldehyde and permeabilization with 0.5% Triton X100 in PBS.

Example 10 a) Immunohistochemistry

Paraffin tissue sections were first deparaffinized and then treated with 0.3% Triton X100 in PBS for antigen retrieval. Kryostat sections were fixed in cold acetone. The the sections were treated 30 min at with 3% $H_2O_2$ and 10% methanol for quenching of endogenous peroxidase. After blocking with 1% BSA-PBS the primary antibody was added at a concentration of 2 μg/ml and incubated for 1 h at RT. For the scFv a secondary mouse-anti-c-myc antibody was added for 1 h at RT. Then a biotinylated goat-anti-mouse antibody was incubated for 30 min at RT and finally developed with ABC-reagent (Vectastain).

b) Western Blot Analysis

Western blot analysis was performed following sodium dodecyl sulfate-polyacrylamide (SDS) gel electrophoresis of purified PSMA and cell lysate from LNCaP cells and transfered to polyvinylidene difluoride membranes. The blots were blocked overnight in PBS containing 5% non-fat milk and incubated with the purified mAbs or scFv at concentrations of 10 μg/ml for 1 h. Then the blots were washed 5 times with PBS-Tween (0.5%) and incubated with horseradish peroxidase conjugated goat anti-mouse IgG for 1 hour at RT. After 5 washes with PBS-Tween (0.5%) the blots were developed by using 3,3',5',5'-tetramethylbenzidine as substrate.

Example 11

Construction, Expression and Purification of scFv-PE40 Proteins

The toxin used in our approach was the truncated version of *Pseudomonas* exotoxin (PE40), lacking domain Ia and containing only domains Ib, II, and III [Pastan et al., J. Biol. Chem. (1989), p. 15157-15160]. The DNA with the coding region in the vector pSW200 was obtained from Prof. W. Wels, Frankfurt [Wels et al., Biotechnology (1992), p. 1128-1132]. The DNA fragment from by position 253 to 613 encoding PE40 was amplified by PCR from plasmid pSW200. The amplified DNA was then ligated into the vector pHOG-His-scFv in a C-terminal position to the scFv using the restriction site XbaI. All cloning steps were performed according to standard methods in *E. coli* XL1 blue and the products were confirmed by sequencing.

Protein induction of the immunotoxin and purification by IMAC was the same like the scFv. The products were tested and characterized by SDS-page, western blot and flow cytometry.

Example 12

Cytotoxicity of scFv-PE40 Immunotoxins

The metabolism of the red tetrazoilium salt WST to a water soluble formazan dye was determined according to the manufacturer's instructions (Boehringer). Target cells (LNCaP and DU 145 as control) were seeded at $2.5 \times 10^4$/well of a 96-well plate and grown for 24 hours until a confluent cell layer was formed. Various dilutions of the recombinant immunotoxins in aliquots of 50 μl/well were added and the plates were incubated for 48 hours at 37° C., 5% $CO_2$. After this time the cultures were pulsed with 15 μl/well WST reagent and incubated for 90 min at 37° C., 5% $CO_2$. Then the spectrophotometrical absorbances of the samples were measured at 450 nm (reference 690 nm). The immunotoxin concentration required to achieve a 50% reduction in cell viability relative to that of untreated control cultures (50% inhibitory concentration=IC50) was calculated.

Figure 11:
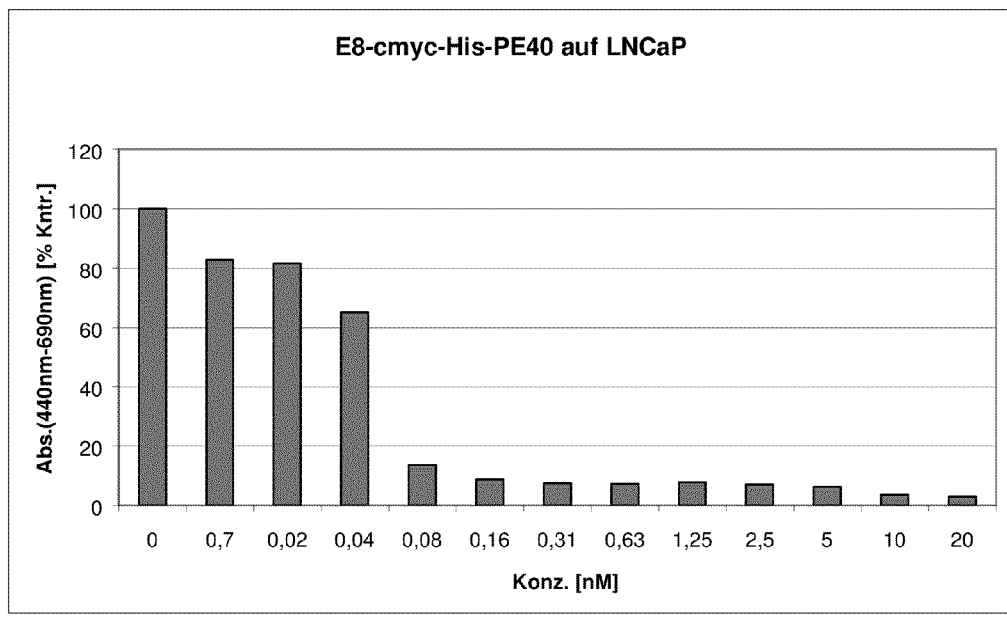
FIG. 11: Cytotoxic effect of recombinant immunotoxin E8-P40 on LNCaP cells
Figure 12:
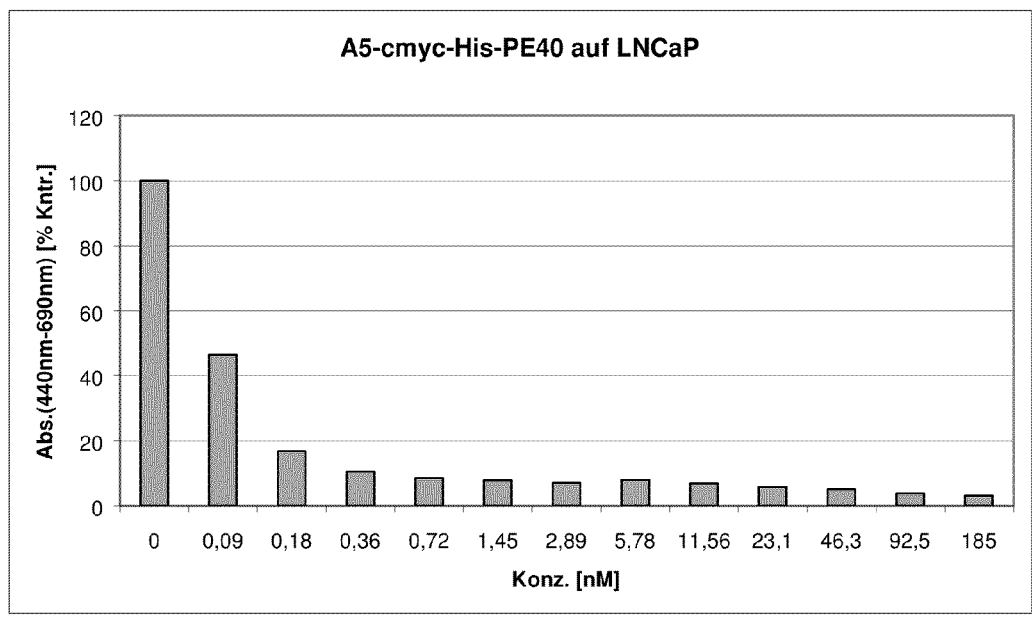
FIG. 12: Cytotoxic effect of recombinant fusion protein A5-P40 on LNCaP cells

Cytotoxicity assays (WST) with the immunotoxins E8-P40 and A5-P40 were prepared with PSMA expressing LNCaP cells and DU 145 control cells. As shown in FIG. 11 a high cytotoxic effect could be shown with the immunotoxin E8-PE40 on LNCaP cells with a IC50 value of 0.05 nM. In FIG. 12 the cytotoxic effect of the immunotoxin A5-PE40 is shown with an IC50 of about 0.09 nM. The cytotoxic background on not PSMA expressing DU 145 cells was 5% for the E8 construct and only 0.01% for the A5 construct evidencing a very good therapeutic window.

Example 13

Generation of the scFv H12 and D7 from mAb 3/F11 and 3/E7

From each mAb a scFv expression library in the phagemid pSEX was generated as described in Example 5.

LNCaP cells and showed a broad distribution, which may correspond to varying PSMA molecules on the cell surface of the former.

c) Immunofluorescence Cytology

Immunofluorescence cytology was prepared as described in Example 4. After detection with a laser scanning confocal microscope a strong binding of the scFv to LNCaP cells and also an internalization into these cells was observed.

d) ELISA and Western Blotting

Binding of the scFv H12 and D7 to purified PSMA in an solid phase ELISA and by Western blotting was weak.

The sequences (amino acid and nucleic acid) of H12 and D7 are given in FIG. 20 and FIG. 21.

TABLE 3

Characteristics of the anti-PSMA scFv H12 and D7

| scFv | Original mAb | FACS on LNCaP MFI* | FACS on PSMA-transfected BOSC (MFI*) | Blot on PSMA | SEQ ID NO of nucleic acid sequence (coding strand) | SEQ ID NO of amino acid sequence | SEQ ID NO of nucleic acid sequence (complementary strand) |
|---|---|---|---|---|---|---|---|
| H12 | 3/E7 | 70 | 25 | 100 kD | 19 | 20 | 23 |
| D7 | 3/F11 | 40 | 24 | 100 kD | 21 | 22 | 24 |

*MFI = Mean fluorescence intensity values at saturating conditions after subtraction of the background staining with an irrelevant isotype-matched control antibody or anti-mouse immunoglobulin alone.

Production and selection of antibody-displaying phage was done according to Example 6.

After six panning rounds alternatively on PSMA and LNCaP cells one specific positive clone was obtained, from mAB 3/E7, which was named H12 and one positive clone was obtained form from mAB 3/F11, which was named D7. The coding region of each scFv was transferred into the expression vector pHOG-21.

ScFv expression and purification was done as described in Example 7.

Example 14

Characterization of the scFv H12 and D7 a) Flow Cytometry on PSMA-Positive and -Negative Cell Lines

The scFvs H12 and D7 reacted with viable LNCaP cells as measured by flow cytometry.

Figure 15:
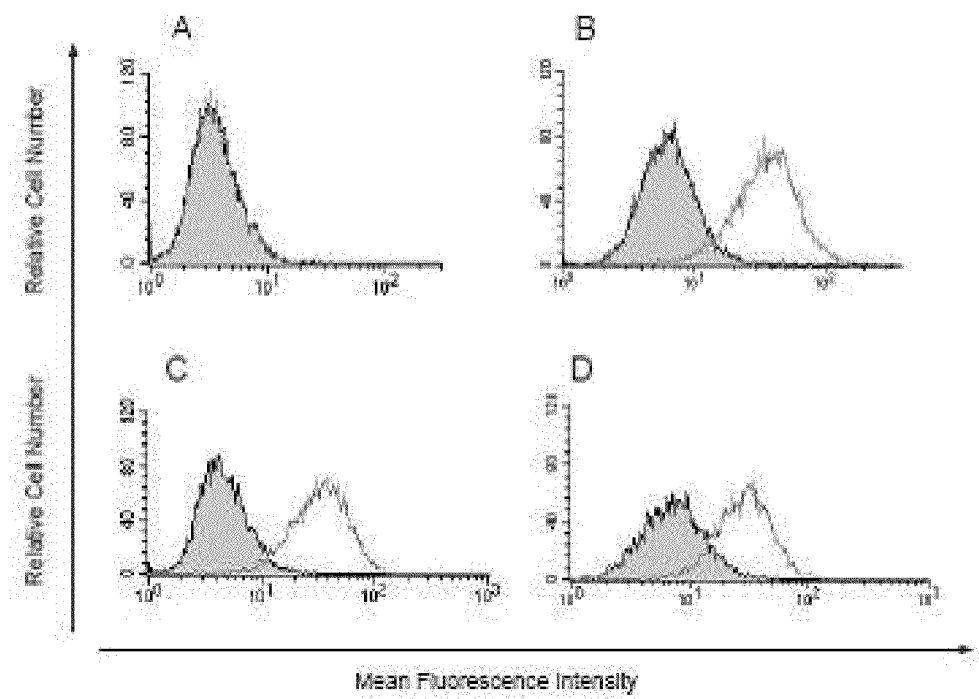
FIG. 15: This Figure shows binding of the scFv A5, H12 and D7 to PSMA-negative DU145 cells (A) and PSMA-positive LNCaP cells (A5=B, H12=C, D7=D). Cells were stained with the mAbs and a PE-conjugated anti-mouse IgG mAb. Histogramms represent logarithms of PE fluorescence on flow cytometer. Negative control was done with secondary antibody only.

From the saturation curves the antibody concentration reaching 50% saturation of PSMA sites was determined to be approximately 120 nM (H12) and 20 nM (D7) respectively. At saturating concentrations MFI values of 70 (H12) and 40 (D7) were reached (FIG. 15).

To evaluate the PSMA binding specificity of the scFv H12 and D7, PSMA-negative prostate cancer cells of DU145 and PC3 and other PSMA negative cell lines (HeLa, MCF7, HCT15 and Jurkat) were additionally stained and analyzed by flow cytometry. All three scFv did not stain the PSMA-negative cells.

b) Flow Cytometry on PSMA Transfectants

Figure 16:
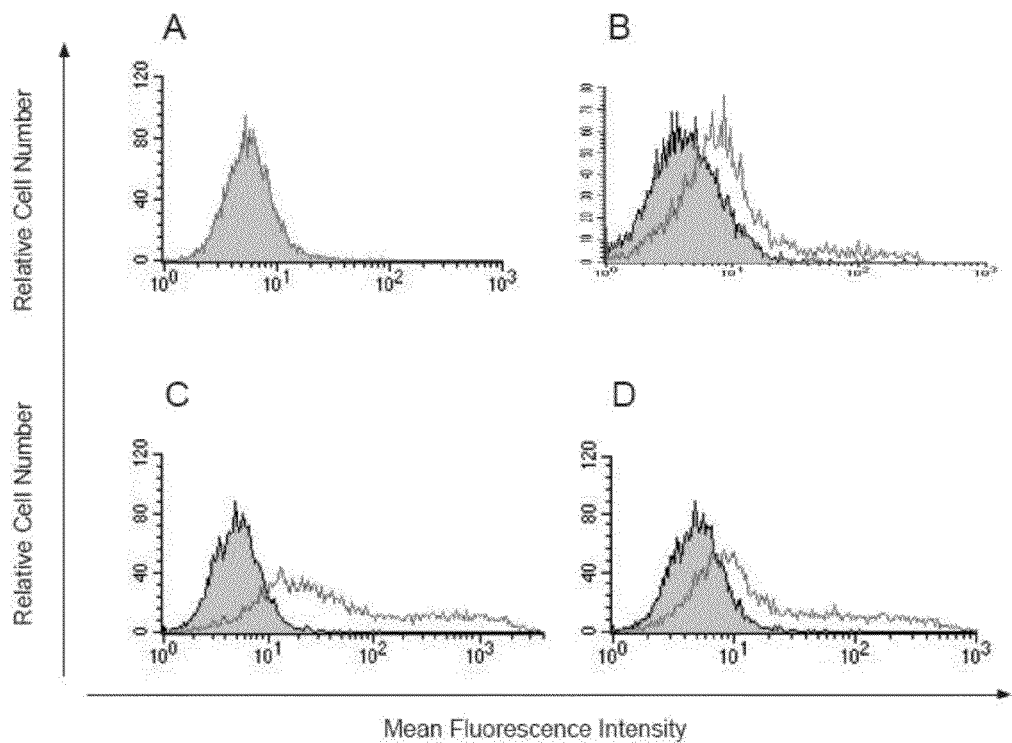
FIG. 16: The binding of the scFv A5, H12 and D7 to PSMA-negative BOSC cells (A) and PSMA-transfected BOSC cells (A5=B, H12=C, D7=D). Cells were stained with the scFv anti-c-myc mAb and PE-conjugated anti-mouse Ig. Histogramms represent logarithms of PE fluorescence on flow cytometer. Negative control was done with secondary antibody only.

To verify a PSMA-specific binding, the scFv H12 and D7 were also tested on BOSC-23 cells transfected with PSMA. Both scFv showed a concentration dependent binding to BOSC cells transfected with full-length PSMA but not to non-transfected cells (FIG. 16). Saturating conditions were reached at 100 nM (D7) and 200 nM (H12). Similar to the mAbs, MFI-values on the transfectants were lower than on Example 15

Construction and Cytotoxicity of a H12-PE40 Immunotoxin and D7-PE40 Immunotoxin

Construction of the H12-PE40 and the D7-PE40 immunotoxin was similar to A5 and E8 immunotoxins described in example 11. PE-40 represents the *Pseudomonas* exotoxic fragment.

Cytotoxicity was tested as described in example 12.

The imunotoxin promoted death of LNCaP cells in a time-dependent manner; highest cytotoxic effects could be observed after 48 h incubation.

Figure 17:
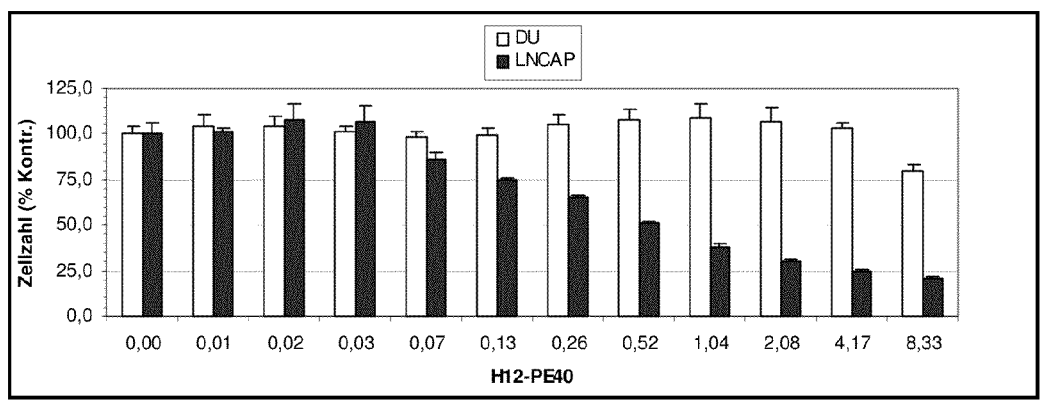
FIG. 17: demonstrates the cytotoxic effect of recombinant immunotoxine HE12-PE40 on LNCaP (black) and DU cells (white).

At this time IC50 values of about 200 μM were found for H12-PE40 and D7-PE40 (FIG. 17).

Additionally, cytotoxicity of H12-PE40 and D7-PE40 was tested on the PSMA-negative cell lines DU 145, PC-3, MCF7 and HCT 15. No cytotoxicity was found on these cell lines at concentrations up to 25 000 μM.

Example 16

Construction of an Anti-PSMA/CD3 Diabody

Figure 18:
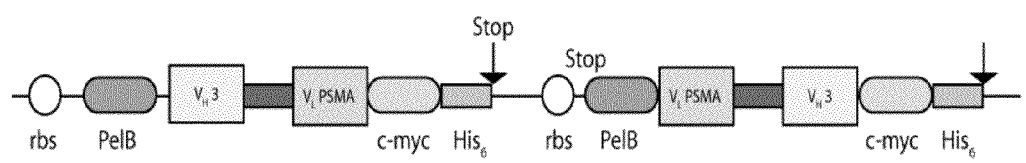
FIG. 18: shows schematically the construction scheme of the A5-CD3 diabody.

A bispecific diabody specific for PSMA and the CD3 chain of the T cell receptor complex was generated. The bispecific diabody was expressed in *E. coli* using a vector containing the dicistronic operon for cosecretion of VhCD3-VlA5 and VhAS-VlCD3 scFv (FIG. 18). For the anti-A5/CD3 diabody construction the plasmids pKID19×3 and pKID 3×19 were used [Kipriyanov, Int. J. Cancer 1998, pp 763]. Bacterial periplasmatic expression and purification was similar to the scFv.

Example 17

Induction of Specific Cytotoxicity by Diabody A5-CD3

The ability of the bispecific diabody to induce tumor cell lysis by redirecting T cell-mediated cytotoxicity was investigated using PBMC from healthy donors as effector cells.

After incubation with or without IL-2 for 4 days, the cells were added to LNCaP target cells, which were seeded at $1.5 \times 10^4$ cells/well of a 96-well plate. The effector-target ratio was 10:1. Diabody was added at different concentrations. After incubation of 48 hours the cultures were pulsed with 15 µl/well WST reagent and incubated for 90 min at 37° C. and 5% $CO_2$. Then the spectrophotometrical absorbances of the samples were measured at 450 nm (reference 690 nm).

Figure 19:
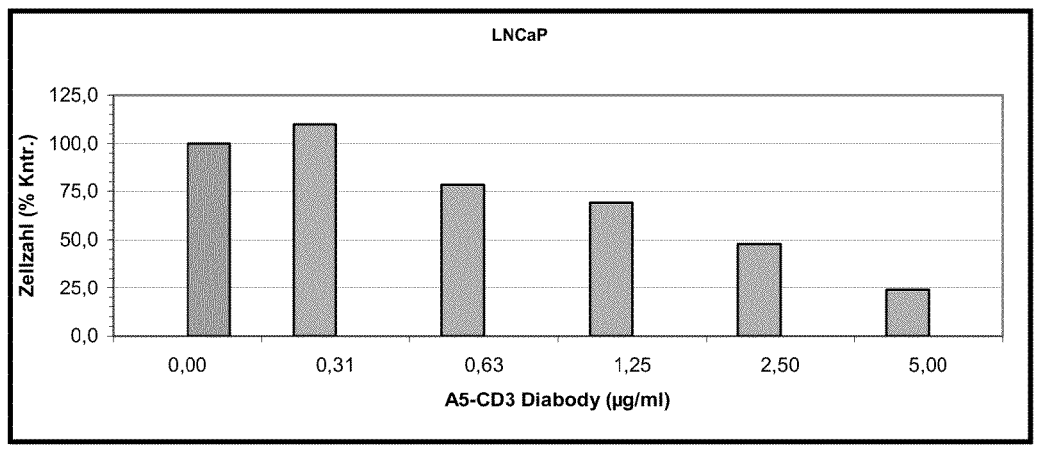
FIG. 19: shows the cytotoxic effect of a diabody constructed from scFv A5 (A5/CD3) at different concentrations and peripheral blood lymphocytes (effect or target ratio 10:1) on LNCaP cells after 48 h incubation.

In this in vitro test the diabody appeared to be quite potent in retargeting activated and inactivated PBMC to lyse the target LNCaP cells in a concentration dependent manner (FIG. 19).

Example 18

Diabody A5-A5

This bivalent monospecific diabody was generated similar to the A5-CD3 diabody (example 16). Bacterial periplasmatic expression and purification was similar to the scFv.

By flow cytometry a strong and specific binding of diabody A5-A5 to LNCaP cells could be shown.

The invention claimed is:

1. An antigen binding portion of an isolated monoclonal antibody which
   a) binds to prostate specific membrane antigen in its native form occurring on the surface of tumor cells
   b) binds strongly to LNCAP cells but not or only minimally to cells which lack expression of prostate specific membrane antigen,
   c) comprises at least three sequences selected from the group consisting of SEQ ID NO:11, SEQ ID NO:12, SEQ ID NO:13, SEQ ID NO:14, SEQ ID NO:15, and SEQ ID NO:16, and
   d) is part of a diabody which binds to T-cell receptor complex.

2. The antigen binding portion according to claim 1 which shows a high binding activity to LNCAP cells reaching 50% saturation of PSMA sites at concentrations between 1 nM and 120 nM.

3. The antigen binding portion according to claim 1, characterized in that said diabody is bispecific for PSMA and the CD3 chain of a T-cell receptor complex.

4. The antigen binding portion according to claim 3, characterized in that said diabody has the ability to induce tumor cell lysis by redirecting T-cells, which results in T-cell mediated cytotoxicity.

5. A pharmaceutical composition comprising an antigen binding portion according to claim 1.

6. A method of treating cancer comprising administering the pharmaceutical composition according to claim 5 to a subject in need thereof.

* * * * *